US009347943B2

(12) United States Patent
Levet et al.

(10) Patent No.: US 9,347,943 B2
(45) Date of Patent: May 24, 2016

(54) PROTEINS USED FOR THE DIAGNOSIS OF LYME BORRELIOSIS

(75) Inventors: Lionel Levet, Oullins (FR); Odile Mejan-Letourneur, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 38 days.

(21) Appl. No.: 13/388,178

(22) PCT Filed: Aug. 26, 2010

(86) PCT No.: PCT/FR2010/051780
§ 371 (c)(1),
(2), (4) Date: Jan. 31, 2012

(87) PCT Pub. No.: WO2011/023909
PCT Pub. Date: Mar. 3, 2011

(65) Prior Publication Data
US 2012/0135027 A1 May 31, 2012

(30) Foreign Application Priority Data

Aug. 28, 2009 (FR) ..................................... 09 04093

(51) Int. Cl.
G01N 33/569 (2006.01)
C07K 14/20 (2006.01)
A61K 39/00 (2006.01)
C07K 14/195 (2006.01)

(52) U.S. Cl.
CPC ........ G01N 33/56911 (2013.01); C07K 14/195 (2013.01); A61K 39/00 (2013.01); G01N 2333/20 (2013.01); G01N 2469/20 (2013.01)

(58) Field of Classification Search
None
See application file for complete search history.

(56) References Cited

U.S. PATENT DOCUMENTS

| 5,620,862 | A | * | 4/1997 | Padula | ........................ 435/7.32 |
| 6,475,492 | B1 | | 11/2002 | Philipp et al. | |
| 6,808,711 | B2 | * | 10/2004 | Motz et al. | ................. 424/190.1 |
| 2009/0162875 | A1 | | 6/2009 | Dattwyler et al. | |

FOREIGN PATENT DOCUMENTS

| WO | WO 00/78800 | A2 | | 12/2000 |
| WO | WO 00/78966 | A1 | * | 12/2000 |
| WO | WO 0078800 | A2 | * | 12/2000 |

OTHER PUBLICATIONS

Greenspan et al. Nature Biotechnology 7: 936-937, 1999.*
Randall et al. Vaccine 11: 1247-1252, 1993.*
Jan. 12, 2011 International Search Report Issued in International Application No. PCT/FR2010/051780.
Jan. 12, 2011 International Search Report Issued in International Application No. PCT/FR2010/051787 (original and English language version).
Jan. 12, 2011 Written Opinion Issued in International Application No. PCT/FR2010/051787 (original and English language version).
Skogman, et al., "Improved Laboratory Diagnostics of Lyme Neuroborreliosis in Children by Detection of Antibodies to New Antigens in Cerebrospinal Fluid," The Pediatric Infectious Disease Journal, (2008), vol. 27, No. 7, pp. 605-612.
Panelius, et al., "Diagnosis of Lyme Neuroborreliosis with Antibodies to Recombinant Proteins DbpA, BBK32, and OspC, and VlsE $IR_6$ Peptide," Journal of Neurology, (2003), vol. 250, No. 11, pp. 1318-1327.
Marangoni, et al. "*Borrelia burgdorferi* VlsE Antigen for the Serological Diagnosis of Lyme Borreliosis," Eur. J. Clin. Microbiol. Infect. Dis., (2008) vol. 27, No. 5, pp. 349-354.
Tjernberg, et al., "Antibody Responses to Borrelia $IR_6$ Peptide Variants and the C6 Peptide in Swedish Patients with Erythema Migrans," International Journal of Medical Microbiology, (2009), vol. 299, No. 6, pp. 439-446.
Steere, et al., "Prospective Study of Serologic Tests for Lyme Disease," Clinical Infectious Diseases, (2008), vol. 47, pp. 188-195.
Göttner, et al., "Heterogeneity of the Immunodominant Surface Protein VlsE among the Three Genospecies of *Borrelia burgdorferi* Pathogenic for Humans," Int. J. Med. Microbiol., (2004), vol. 293, Suppl. 37, pp. 172-173.
Arnaud, et al., "Construction and Expression of a Modular Gene Encoding Bacteriophage T7 RNA Polymerase," Gene, (1997), vol. 199, pp. 149-156.
Bretz, et al., "Specificities and Sensitivities of Four Monoclonal Antibodies for Typing of *Borrelia burgdorferi* Sensu Lato Isolates," Clinical and Diagnostic Laboratory Immunology, (2001), vol. 8, No. 2, pp. 376-384.
Ryffel, et al., "Scored Antibody Reactivity Determined by Immunoblotting Shows an Association between Clinical Manifestations and Presence of *Borrelia burgdorferi* sensu stricto, *B. garinii*, *B. Afzelii*, and *B. Valaisiana* in Humans," Journal of Clinical Microbiology, (1999), vol. 37, No. 12, pp. 4086-4092.
U.S. Appl. No. 13/388,168 in the name of Levet et al., filed Jan. 31, 2012.
Mikayama et al., "Molecular cloning and functional expression of a cDNA encoding glycosylation-inhibiting factor," Proc. Natl. Acad. Sci. USA, vol. 90, pp. 10056-10060, Nov. 1993.
Greenspan et al., "Defining epitopes: It's not as easy as it seems," Nature Biotechnology, vol. 17, pp. 936-937, Oct. 1999.
Chothia et al., "The relation between the divergence of sequence and structure in proteins," The EMBO Journal, vol. 5 No. 4, pp. 823-826, 1986.
Rudinger, "Characteristics of the amino acids as components of a peptide hormone sequence," Peptide Hormones, pp. 5-7, Jun. 1976.
Sep. 9, 2013 Office Action issued in U.S. Appl. No. 13/388,168.
May 2, 2014 Office Action issued in U.S. Appl. No. 13/388,168.

* cited by examiner

*Primary Examiner* — S. Devi
(74) *Attorney, Agent, or Firm* — Oliff PLC

(57) ABSTRACT

Chimera proteins including: (i) at least one sequence of a DbpA protein of a *Borrelia* species selected from *B. afzelii*, *B. burgdorferi* sensu stricto and *B. garinii*, and (ii) at least one sequence of an OspC protein of a *Borrelia* species selected from *B. afzelii*, *B. burgdorferi* sensu stricto and *B. garinii*. Also, a method and a kit for the in vitro diagnosis of Lyme borreliosis using said proteins.

25 Claims, No Drawings

PROTEINS USED FOR THE DIAGNOSIS OF LYME BORRELIOSIS

Lyme borreliosis (LB) is a noncontagious infectious disease caused by a spirochete called *Borrelia burgdorferi*, which is transmitted to humans via a bite by a tick of the genus *Ixodes*. Without treatment, LB leads to various pathological disorders (dermatological, arthritic, cardiac, neurological and sometimes ocular disorders). It is the most common vector-borne disease in the USA and in certain temperate countries of the northern hemisphere.

Several *borrelia* species, currently denoted under the group term *burgdorferi* or *Borrelia burgdorferi* sensu lato (including *Borrelia burgdorferi* sensu stricto, *B. garinii* and *B. afzelii*), are involved in this infection. These species are pathogenic to humans.

In the United States, the infectious species involved is *Borrelia burgdorferi* sensu stricto. In Europe, in addition to this species, *B. garinii* and *B. afzelii* are involved. In Asia, the species involved are *B. garinii* and *B. afzelii*.

In the United States, approximately 10 000 cases per year are reported. In Europe, the incidence rates vary from less than 5 per 100 000.

Lyme borreliosis progresses by passing through three distinct phases, from early infection to the late phase. The early stage (stage I) may be asymptomatic or reflected by flu-like symptoms. In 50-80% of cases, the appearance of an inflammatory skin rash with a very particular appearance, called erythema migrans (EM) is noted several days after the bite by the tick. In the absence of treatment, the dissemination of the *Borrelia* via the blood is reflected a few weeks later by the occurrence of inflammatory arthritis, neurological (neuroborreliosis) and meningeal involvement, and skin and cardiac manifestations (stage II). After several months or years, the disease progresses to a chronic atrophicans form, encephalopathy, encephalomyelitis and chronic arthritis (stage III).

A particular organotropism exists for each of the species of *Borrelia burgdorferi*. While the first stage of erythema migrans is without distinction linked to the three species, the progression to a neurological form is preferentially associated with the species *B. garinii*, arthritis is more associated with *B. burgdorferi* sensu stricto, and acrodermatitis chronica atrophicans is specific for *B. afzelii*.

The similarity of the clinical symptoms between Lyme borreliosis and other unrelated diseases, and also the variability in manifestations, makes clinical diagnosis difficult. The diagnosis of borreliosis can be particularly difficult on the basis of clinical observations, if case history evidence is absent (tick bite or EM). The early stage of the disease may be without visible symptoms up to the time it reaches very advanced clinical stages.

Consequently, the diagnosis of LB is based on clinical signs but also on the detection of pathogenic *Borrelia burgdorferi*-specific antibodies in the serum, most commonly by ELISA (Enzyme Linked ImmunoSorbent Assay) or else EIA or IFA. The anti-*Borrelia burgdorferi* IgM antibodies generally appear a few days or weeks after the beginning of the infection and can persist during the progression of the disease. The IgG response is later. Most patients have IgGs approximately one month after the beginning of the active infection and these IgGs can also persist for years after the initial exposure and resolution of the symptoms.

In Europe, the evaluation of the serological response is complicated owing to the existence of three pathogenic species and to the interspecies variability for the major immunodominant antigens. The antigens currently routinely used for detecting LB IgGs and IgMs are ultrasound-treated cell samples of *Borrelia burgdorferi* sensu lato. The performance levels of the serological assays with these antigens, in terms of specificity and sensitivity, are highly variable. Thus, owing to insufficient specificity, involving cross reactivities with antibodies associated with various pathogenic bacteria, in particular *Treponema pallidum* (etiological agent for syphilis), spirochetes, *rickettsiae, ehrlichia,* or *Helicobacter pylori*, the diagnosis of samples having tested positive by ELISA must be confirmed by immunoblotting. Sensitivity is also a major factor. This is because *Borrelia burgdorferi* sensu lato expresses various surface proteins via adaptation to various microenvironments, such that the genetic diversity and the differential expression of the *Borrelia burgdorferi* genes in patients have important implications for the development of serological tests for LB. The OspC (Outer-surface protein C) lipoprotein and the DbpA (Decorin-binding protein A) protein are among these proteins. DbpA appears to be mainly expressed in mammals after infection. These proteins exhibit great sequence variability according to *Borrelia burgdorferi* species and great interspecies sequence variability. The DbpA proteins are particularly variable and are divided up into four groups: a group corresponding to the genospecies *Borrelia afzelii*, another group corresponding to the genospecies *Borrelia* sensu stricto and two groups corresponding to the genospecies *Borrelia burgdorferi garinii*. The interspecies amino acid sequences identity between the DbpA proteins is only 40-44%. It is 54-72% for the OspC proteins.

It is therefore necessary to develop a kit which meets the expected specificity and sensitivity criteria and in particular which improves IgM detection, in terms of sensitivity, in the case of recent infection.

The present invention proposes to solve all the drawbacks of the prior art through novel chimeric recombinant proteins which can be readily synthesized and purified and which exhibit strong immunoreactivity with respect to sera from patients that may be infected with one or more pathogenic species of *Borrelia burgdorferi*. These chimeric fusion proteins make it possible to overcome the problems of sensitivity and specificity linked: to the presence of several pathogenic species of *Borrelia burgdorferi*, to the great sequence variability of the surface antigens of *Borrelia burgdorferi* and to the need to use several antigens representative of the species *B. garinii, B. burgdorferi* sensu stricto and *B. afzelii* in order to develop a test for the diagnosis of Lyme borreliosis based at least on the detection of anti-OspC and anti-DbpA antibodies.

The chimeric fusion proteins of the invention make it possible, moreover, to solve difficulties encountered in expressing certain antigens in recombinant form at a high level. Indeed, despite considerable work on the construction of genes in order to obtain optimized expression thereof in *E. coli*, the inventors have shown for the first time that the OspC proteins are weakly expressed in recombinant form in *E. coli*, whereas, entirely unforeseeably, they have found that the DbpA proteins can be expressed under the same conditions in soluble form under nondenaturing conditions and with higher yields. The ease of expression of the DbpA proteins has been exploited in order to create chimeric proteins composed of DbpA and of OspC, and the inventors have been able to show that the chimeric proteins are expressed better than the isolated OspC proteins, which was completely unexpected since it has never been described or even suggested that the DbpA proteins can have fusion protein properties. Thus, in order to improve the expression levels, the inventors have designed DbpA-OspC chimera proteins using the unexpected fusion properties of the DbpA proteins in order to improve the expression and the solubility of the chimera proteins. Preferably, in the molecular construct for the expression of a chimera protein of the invention, the gene encoding the DbpA protein is integrated upstream of that or of those encoding one or more OspC proteins. According to this preferred molecular construct, the chimera protein of the invention has, at its N-terminal end, a sequence belonging to a DbpA protein sequence and, at its C-terminal end, a sequence belonging to an OspC protein sequence. In addition to making it possible to facilitate and optimize the expression and the solubility of the chimera protein, this type of preferential construct also has another advantage, which is that of improving the recognition of the chimera by anti-*Borrelia* antibodies owing to the better presentation, to said antibodies, of the immunodominant region of the OspC protein. A further advantage of the chimeric proteins of the invention is that of limiting the number of recombinant proteins that go to make up a kit for the diagnosis of Lyme borreliosis. Moreover, the fusion properties of the DbpA proteins make them an excellent candidate for the expression of DbpA-OspC chimera vaccine proteins for preventing a *Borrelia* infection. Consequently, the chimeric proteins of the invention are of use as an active agent in a preventive vaccine against borreliosis.

Thus, the subject of the present invention is an unnatural, *Borrelia* DbpA-OspC chimeric fusion protein, which is synthetic, i.e. obtained by genetic engineering (recombinant protein) or by peptide synthesis, said protein being selected from the group consisting of:

(a) a protein of which the amino acid sequence comprises (or consists of) the sequence SEQ ID NO: 1 and the sequence SEQ ID NO: 2 or a variant of said protein of which the amino acid sequence comprises (or consists of) a sequence which exhibits at least 40% identity with SEQ ID NO: 1 and a sequence which exhibits at least 50% identity with SEQ ID NO: 2, on the condition that said variant is capable of forming an immunological complex with antibodies produced following a *Borrelia* infection or that said variant is capable of inducing the production of anti-*Borrelia* antibodies;

(b) a protein of which the amino acid sequence comprises (or consists of) the sequence SEQ ID NO: 3 and the sequence SEQ ID NO: 4 or a variant of said protein of which the amino acid sequence comprises (or consists of) a sequence which exhibits at least 40% identity with SEQ ID NO: 3 and a sequence which exhibits at least 50% identity with SEQ ID NO: 4, on the condition that said variant is capable of forming an immunological complex with antibodies produced following a *Borrelia* infection or that said variant is capable of inducing the production of anti-*Borrelia* antibodies;

(c) a protein of which the amino acid sequence comprises (or consists of) the sequence SEQ ID NO: 5 and the sequence SEQ ID NO: 7 or a variant of said protein of which the amino acid sequence comprises (or consists of) a sequence which exhibits at least 40% identity with SEQ ID NO: 5 and a sequence which exhibits at least 50% identity with SEQ ID NO: 7, on the condition that said variant is capable of forming an immunological complex with antibodies produced following a *Borrelia* infection or that said variant is capable of inducing the production of anti-*Borrelia* antibodies;

(d) a protein of which the amino acid sequence comprises (or consists of) the sequence SEQ ID NO: 6 and the sequence SEQ ID NO: 7 or a variant of said protein of which the amino acid sequence comprises (or consists of) a sequence which exhibits at least 40% identity with SEQ ID NO: 6 and a sequence which exhibits at least 50% identity with SEQ ID NO: 7, on the condition that said variant is capable of forming an immunological complex with antibodies produced following a *Borrelia* infection or that said variant is capable of inducing the production of anti-*Borrelia* antibodies;

(e) a protein of which the amino acid sequence comprises (or consists of) the sequence SEQ ID NO: 5, the sequence SEQ ID NO: 6 and the sequence SEQ ID NO: 7 or a variant of said protein of which the amino acid sequence comprises (or consists of) a sequence which exhibits at least 40% identity with SEQ ID NO: 5, a sequence which exhibits at least 40% identity with SEQ ID NO: 6 and a sequence which exhibits at least 50% identity with SEQ ID NO: 7, on the condition that said variant is capable of forming an immunological complex with antibodies produced following a *Borrelia* infection or that said variant is capable of inducing the production of anti-*Borrelia* antibodies; and (f) a protein of which the amino acid sequence comprises (or consists of) a sequence selected from SEQ ID NOs: 8, 9, 10, 11, 12, 13 and 14.

Each of the proteins identified above comprises at least one sequence of the extracellular domain of a DbpA protein of a *Borrelia* species selected from *B. afzelii* (SEQ ID NO: 1), *B. burgdorferi* sensu stricto (SEQ ID NO: 3) and *B. garinii* (group III: SEQ ID NO: 5) (group IV: SEQ ID NO: 6) or a sequence exhibiting at least 40% identity with said sequences, and at least one sequence of an OspC protein of *B. afzelii* (SEQ ID NO: 2), *B. burgdorferi* sensu stricto (SEQ ID NO: 4) and *B. garinii* (SEQ ID NO: 7) or a sequence which exhibits at least 50% identity with said sequences. Preferentially, the DbpA sequence(s) is (are) placed on the N-terminal side of the chimeric recombinant protein and the OspC sequence is placed on the C-terminal side of the chimeric recombinant protein.

A sequence of at least 6 histidines can be added at the N-terminal or C-terminal end of the chimeric protein in order to enable its purification on metal-chelate resin. The 6-histidine sequence, identified in SEQ ID NO: 22, is preferentially placed on the N-terminal side of the construct. This is illustrated, by way of example, by the sequences SEQ ID NOs: 9, 11, 13 and 14 which comprise a poly-His(6) tail on the N-terminal side. The poly-His tail can be encoded by any one of the sequences identified in SEQ ID NOs: 23, 24 and 25.

Additional amino acids may be present upstream of the poly-His tail owing to the insertion, into the coding DNA sequence, of a small sequence which makes it possible to facilitate the cloning of the sequence of interest into the expression plasmid. This is in particular the case in the sequences SEQ ID NOs: 9, 11, 13 and 14 which comprise an "MRGS" motif (SEQ ID NO: 26) upstream of the poly-His tail. The "MRGS" motif is encoded by ATGAGGGGATCC (SEQ ID NO: 27).

A linking region can be introduced between each of the DbpA and OspC sequences which makes up a chimeric recombinant protein. This type of region corresponds to a flexible spacing region providing better accessibility of the potential antibodies to each of the domains. It is rich in Gly and Ser amino acids, which are amino acids described as providing flexibility in the tertiary structure of the protein. It is also possible to introduce, into a coding sequence of interest, a DNA arm (or linker) in order to promote the linking between the coding sequences for two proteins of interest. This is in particular the case in the sequence SEQ ID NO: 14 which comprises a "GSGG" motif (SEQ ID NO: 28) encoded by sequence GGTTCCGGGGGT (SEQ ID NO: 29), which acts as a linker arm between the DbpA group IV and OspC proteins of *B. garinii*.

The preferred proteins are identified in SEQ ID NOs: 8, 9, 10, 11, 12, 13 and 14. They are respectively encoded by the corresponding DNA sequences identified in SEQ ID NOs: 15, 16, 17, 18, 19, 20 and 21.

The subject of the invention is also the DNA sequences encoding the proteins as defined above, and in particular the sequences identified in SEQ ID NOs: 15, 16, 17, 18, 19, 20 and 21.

The subject of the invention is also an expression cassette which is functional in a cell derived from a prokaryotic organism (example: *Escherichia coli*) or a eukaryotic organism, such as a yeast (example: *Pichia, Schizosaccharomyces*), allowing the expression of the nucleic acid described above (DNA), when it is placed under the control of the elements allowing its expression, and also the vector comprising such a cassette.

The proteins of the invention can in particular be used for the diagnosis of a *Borrelia* infection. Thus, the subject of the present invention is a method for the in vitro diagnosis of Lyme borreliosis in a biological sample (for example a serum, blood, plasma, etc., sample), according to which the biological sample is brought into contact with at least one protein as defined above and it is determined whether there is formation of an immunological complex between said protein and antibodies of the biological sample (IgGs and/or IgMs), for example by addition of at least one anti-human-immunoglobulin labeled with any appropriate label. The term "label" is intended to mean a tracer capable of generating a signal. A nonlimiting list of these tracers comprises enzymes which produce a signal that is detectable for example by colorimetry, fluorescence or luminescence, for instance horseradish peroxidase, alkaline phosphatase, β-galactosidase or glucose-6-phosphate dehydrogenase; chromophores, for instance fluorescent, luminescent or coloring compounds; electron-dense groups that can be detected by electron microscopy or via their electrical properties, for instance conductivity, by amperometry or voltammetry methods, or by impedance measurements; groups that can be detected by optical methods, for instance diffraction, surface plasmon resonance, or contact angle variation, or by physical methods, for instance atomic force spectroscopy, tunnel effect, etc.; radioactive molecules, for instance $^{32}$P, $^{35}$S or $^{125}$I. Preferably, the protein(s) is (are) immobilized on a solid support which may be the tip of a Vidas® apparatus, the well of a microtitration plate, a gel, a particle, etc.

In one embodiment of the invention, the biological sample is in addition brought into contact with at least one VlsE chimeric protein, as described hereinafter.

The VlsE protein (surface expressed lipoprotein with Extensive antigenic Variation) is mainly expressed, in vivo, transiently and rapidly after infection of the host. It is very immunogenic in the infected host, involving the production of IgGs and IgMs. The Vls locus is located on a linear plasmid of 28 kb (lp28-1) present in the three *Borrelia* genospecies responsible for Lyme disease and composed of silent cassettes and an expression site (VlsE). In vivo, random recombinations between expression cassettes and silent cassettes occur during infection and are responsible for the antigenic variability of VlsE. The VlsE protein is composed of six variable regions VR1-VR6, located at the surface of the VlsE protein, spaced out by "invariable" regions IR1-IR6.

The chimeric VlsE protein comprises (or consists essentially of):
(i) at least one sequence selected from the sequences identified in SEQ ID NOs: 30, 31, 32, 33 and 34 and the sequences which exhibit at least 50% identity, preferably 60% or 70% identity and advantageously at least 80% or 85% identity with SEQ ID NOs: 30, 31, 32, 33 and 34, and
(ii) at least one sequence comprising the sequence SEQ ID NO: 35 or a sequence which exhibits at least 80% identity, preferably at least 85% identity and advantageously at least 90% identity with SEQ ID NO: 35, the sequence SEQ ID NO: 36 or a sequence which exhibits at least 80% identity, preferably at least 85% identity and advantageously at least 90% identity with SEQ ID NO: 36, the sequence SEQ ID NO: 37 or a sequence which exhibits at least 80% identity, preferably at least 85% identity and advantageously at least 90% identity with SEQ ID NO: 37, and, optionally, the sequence SEQ ID NO: 43. The VlsE chimeric protein preferably comprises the sequence SEQ ID NO: 43.

As described previously, it is possible to add a poly-histidine(x6) tail at the N-terminal end of the chimeric protein in order to allow its purification on metal-chelate resin, and also additional amino acids upstream of the poly-His tail.

A preferred chimera protein comprises (or consists essentially of or else consists of):
(i) the sequence SEQ ID NO: 30 or a sequence which exhibits at least 50% identity, preferably at least 60% or 70% identity and advantageously at least 80 or 85% identity with SEQ ID NO: 30; and
(ii) the sequence comprising the sequence SEQ ID NO: 35 or a sequence which exhibits at least 80% identity, preferably at least 85% identity and advantageously at least 90% identity with SEQ ID NO: 35, the sequence SEQ ID NO: 36 or a sequence which exhibits at least 80% identity, preferably at least 85% identity and advantageously at least 90% identity with SEQ ID NO: 36, the sequence SEQ ID NO: 37 or a sequence which exhibits at least 80% identity, preferably at least 85% identity and advantageously at least 90% identity with SEQ ID NO: 37, and the sequence SEQ ID NO: 43.

The preferred chimera protein comprises (or consists essentially of or else consists of):
(i) the sequence SEQ ID NO: 30; and
(ii) the sequence comprising the sequences SEQ ID NOs: 35, 36, 37 and 43.

The protein comprises or consists of a sequence identified as SEQ ID NO: 38.

SEQ ID NO: 30 corresponds to the sequence of the VlsE extracellular domain of *B. garinii* (strain pBi) deleted of its signal sequence (aa 1-19) and of the C-terminal region of the mature protein located after the IR6 domain.

SEQ ID NO: 31 corresponds to the sequence of the VlsE extracellular domain of *B. garinii* (strain pBr) deleted of its signal sequence and of the C-terminal region of the mature protein located after the IR6 domain.

SEQ ID NO: 32 corresponds to the sequence of the VlsE extracellular domain of *B. garinii* (strain pLi) deleted of its signal sequence and of the C-terminal region of the mature protein located after the IR6 domain.

SEQ ID NO: 33 corresponds to the sequence of the VlsE extracellular domain of *B. afzelii* (strain pKo) deleted of its signal sequence and of the C-terminal region of the mature protein located after the IR6 domain.

SEQ ID NO: 34 corresponds to the sequence of the VlsE extracellular domain of *B. burgdorferi* sensu stricto (strain B31) deleted of its signal sequence and of the C-terminal region of the mature protein located after the IR6 domain.

SEQ ID NO: 35 corresponds to the sequence of the IR6 domain of *B. burgdorferi* sensu stricto (strain B31).

SEQ ID NO: 36 corresponds to the sequence of the IR6 domain of *B. afzelii* (strain ACA-1).

SEQ ID NO: 37 corresponds to the sequence of the IR6 domain of *B. garinii* (strain Ip90).

SEQ ID NO: 43 corresponds to the sequence of the VR6 variable region of *B. burgdorferi* sensu stricto (strain B31).

The subject of the invention is also a kit for the in vitro diagnosis of Lyme borreliosis comprising at least one DbpA-OspC chimeric protein as defined above, preferably comprising at least one anti-human-immunoglobulin labeled with any appropriate label corresponding to the definitions given above. The kit may also comprise a chimeric VlsE protein as defined above.

The proteins of the invention can also be used as an active ingredient for the preparation of a vaccine composition for preventing a *Borrelia* infection. Thus, the subject of the present invention is also a vaccine composition comprising at least one protein as defined above and a pharmaceutically acceptable vehicle.

The following examples are given by way of illustration and are in no way limiting in nature. They make it possible to understand the invention more clearly. The order of the sequences encoding the various immunodominant epitope regions of the chimeric recombinant proteins can be optionally modified. The epitopes can also exhibit variations compared with the sequences described in the examples according to the species of *Borrelia burgdorferi* and the strain(s) that they represent. The length of the linking regions can also be modified in order to improve the flexibility between two domains. Finally, the attachment regions can be inserted within the linking regions.

EXAMPLES

Example 1

Preparation of the Plasmid Construct Encoding the DpbA-OspC Chimeric Recombinant Proteins The DNA sequences encoding the various DpbA and OspC sequences described are identified in table 1. The DNA sequences were optimized in order to promote expression in *E. coil* using GeneOptimizer™ and synthesized respectively by GenScript corporation (Scotch Plains, N.J., USA) or GeneArt GmbH (Regensburg, Germany).

TABLE 1

| | Sequence origin | | |
|---|---|---|---|
| | | *B. burgdorferi* species | |
| protein | *B. sensu stricto* | *B. afzelii* | *B. garinii* |
| DbpA | *B31; **aa 2-192; ***AF069269 | *PKo; **aa 2-150; ***AJ131967 | *40; **aa 2-187; ***AF441832 *PBi; **aa 2-176; ***AJ841673 |
| OspC | *B31; **aa 26-210; ***X73622 | *PKo; **aa 2-212; ***X62162 | *PEi; **aa 32-208; ***AJ749866 |

*Isolate;
**amino acids (aa);
***GenBank accession No.

Each chimeric recombinant protein comprises at least one epitope region corresponding to the extracellular domain of a DbpA sequence of *Borrelia burgdorferi* sensu stricto or *B. afzelii* or *B. garinii* and at least one epitope region corresponding to the extracellular domain of an OspC sequence of *Borrelia burgdorferi* sensu stricto or *B. afzelii* or *B. garinii*.

The combinations of various nucleotide sequences encoding DbpA and/or OspC sequences and also the modifications of nucleotide sequences, such as deletions, addition of a linking sequence or addition of a linker sequence, were carried out by genetic engineering using the PCR techniques well known to those skilled in the art and described, for example, in Sambrook J. et al., Molecular Cloning: A Laboratory Manual, 1989.

The DNA sequences encoding the chimeric proteins of interest were introduced into the pMR expression vector [2] between the BamHI restriction site in the 5' position and the EcoRI or HindIII site in the 3' position. The plasmid constructs and the corresponding proteins cited as example (bLYM114, bLYM120 and bLYM121) are described in table 2. The presence of MRGS in the N-terminal position of the recombinant proteins and the corresponding nucleotide sequence ATG AGG GGA TCC was introduced by the cloning technique used into the pMR expression vector. Only the ATG start codon and consequently the Met amino acid are really essential in this sequence.

A poly-histidine sequence (6×His) was introduced on the N-terminal side of each recombinant protein. This sequence allows purification of the recombinant proteins on a metal-chelate affinity column. It is a region for attachment to the Ni-NTA gel which makes it possible to subsequently facilitate the step of purifying the chimeric recombinant protein. This HHHHHH peptide (SEQ ID NO: 22) is encoded by the nucleotide sequences CATCATCATCATCATCAT (SEQ ID NO: 23) or CATCATCATCATCATCAC (SEQ ID NO: 24) or CATCATCACCACCATCAT (SEQ ID NO: 25) or by any other sequence encoding the sequence SEQ ID NO: 22. This particular attachment region, comprising a succession of histidines, allows in particular the oriented attachment of the recombinant protein to a support consisting of silica or of metal oxides.

TABLE 2

Plasmid constructs and corresponding proteins

| | Recombinant protein characteristics | | Plasmid construct characteristics | |
|---|---|---|---|---|
| Name | N-terminal Tag | *B. burgdorferi* sequence | Parental vector | Site of insertion of the insert sequence into the vector |
| bLYM114 SEQ ID NO: 9 | 6 × His | *B. afzelii* strain PKo DbpA aa 2-150 + OspC aa 2-212 | pMR78* | 5'BamHI/ 3'EcoRI |
| bLYM120 SEQ ID NO: 11 | 6 × His | *B. sensu stricto* strain B31 DbpA aa 28-192 + OspC aa 26-210 | pMR78* | 5'BamHI/ 3'HindIII |
| bLYM121 SEQ ID NO: 14 | 6 × His | *B. garinii* DbpA III aa 25-187 strain 40 + DbpA IV aa 24-176 strain PBi + OspC aa 32-208 strain PEi | pMR78* | 5'BamHI/ 3'HindIII |

*[2]

Example 2

Expression of the Recombinant Proteins bLYM114, bLYM120 and bLYM121 of Example 1 and Purification A plasmid construct corresponding to a sequence SEQ ID NO: 16, 18 or 21 inserted into an expression vector (pMR) was used to transform an *E. coli* bacterium (strain BL21) according to a conventional protocol known to those skilled in the art. The transformed bacteria were selected by virtue of their ampicillin resistance carried by the pMR vector.

A clone of a recombinant bacterium was then selected in order to inoculate a preculture of 40 ml of 2×YT medium (16 g/l tryptone; 10 g/l yeast extract; 5 g/l NaCl, pH 7.0) containing 100 µg/ml of ampicillin. After 15 to 18 hours of incubation at 30° C. with shaking at 250 rpm, this preculture was used to inoculate 1 liter of 2×YT medium containing 2% glucose and 100 µg/ml of ampicillin. This culture was incubated at 30° C. with shaking at 250 rpm until the OD at 600 nm reaches 1.0/1.2. The culture was maintained for 3 hours 30 min. or 4 hours at 30° C. while adding 0.4 mM isopropyl-β-D-thiogalactopyranoside (IPTG), and harvested by centrifugation at 6000 g for 30 min. The cell pellet was stored at −60° C. For the purification, the wet biomass was thawed and resuspended in a lysis buffer containing protease inhibitors without EDTA (Roche) and benzonase nuclease (Novagen), and subjected to cell rupture at 1.6 kBar in a cell disruptor (Constant Systems Ltd, Daventry, United Kingdom). The lysate was then centrifuged at 10 000 rpm for 45 min. at 2-8° C. The supernatant obtained contains the soluble proteins. This supernatant was filtered through a 0.45µ filter and purified by affinity chromatography on a metal chelation column (nickel-nitrilotriacetic acid matrix (Ni-NTA, Qiagen)). To do this, the supernatant was loaded (1 ml/min) at 18-25° C. onto an 8 ml column of Ni-NTA gel equilibrated in buffer A (see table 3). The column was then washed in buffer A, until an $OD_{280\,nm}=0$ was obtained at the column outlet. The elution of the recombinant protein is obtained by applying a buffer B, according to the indications reported in table 3, and the purified protein was dialyzed in a 10000 ou 20000 MWCO dialysis cassette (Slide-A-Lyser®, Pierce) against a dialysis buffer. The conditions for purification on Ni-NTA gel are described in table 3.

TABLE 3

Recombinant protein purification

| Protein | bLYM114 SEQ ID NO: 14 | bLYM120 SEQ ID NO: 11 | bLYM121 SEQ ID NO: 14 |
|---|---|---|---|
| Lysis and washing buffer | | Buffer A [1] | |
| Elution buffer | | Buffer B [2] | |
| Elution step 1 | 90% buffer A + 10% buffer B (4CV) | 92% buffer A + 8% buffer B (4CV) | 100% buffer B |
| Elution step 2 | 100% buffer B | 100% buffer B | NA |
| Purification yield mg protein/g wet biomass | 12 | 13 | 20 |
| Purification yield mg protein/L of culture | 80 | 122 | 245 |

[1] 50 mM sodium phosphate, 30 mM imidazole, 500 mM NaCl, 0.1% TWEEN 20, 5% glycerol, pH = 7.8
[2] 50 mM sodium phosphate, 325 mM imidazole, 500 mM NaCl, 5% glycerol, pH = 7.5

The samples were analyzed on NuPAGE® Novex® 4-12% in a NuPAGE® MES-SDS buffer, according to the instructions of the producer (Invitrogen). The proteins were either stained with COOMASSIE BRILLIANT BLUE or were transferred electrophoretically onto a nitrocellulose membrane. The membrane was blocked with 5% (w/v) dry milk in PBS and incubated with an antipentahistidine antibody (Qiagen) in PBS containing 0.05% TWEEN 20. A horseradish peroxidase-labeled goat anti-mouse IgG conjugate (Jackson Immunoresearch laboratories) in PBS/TWEEN was used as secondary antibody.

The protein concentration was determined using the Bradford kit (PIERCE COOMASSIE PLUS, Perbio Science) with BSA as protein standard.

Example 3

Detection of Human IgGs and IgMs with the Chimeric Recombinant Proteins Using a Line Immunoblot Technique Each recombinant protein was deposited on a polyvinylidene difluoride membrane (PVDF, Immobilon, Millipore, Bedford, Mass. USA) according to the following protocol: The protein concentration was adjusted to 1 mg/ml in PBS, pH 7.2, and diluted in PBS, pH 7.2, supplemented with 0.03% TWEEN 20 (dilution $1/200^{th}$). The PVDF membrane was wetted in methanol, washed in demineralized water and laid out on a wet blotting paper. A plastic ruler was immersed in the protein dilution and attached to the PVDF membrane. After depositing of the proteins and drying of the membranes, the membranes were cut vertically into narrow strips. Before use, the narrow strips were incubated with 5% gelatin in TBS, pH 7.5, for 1 hour at 37° C. The immunoblot protocols were carried out at ambient temperature as described by Bretz A. G. et al. [3]. The narrow strips were incubated for 2 hours with human sera diluted to $1/200^{th}$ in TBS with 1% gelatin, washed and incubated with an anti-human-IgG or anti-human-IgM antibody labeled with alkaline phosphatase (Sigma, St-Louis, USA) diluted to $1/1000^{th}$ in TBS with 1% gelatin. After washing, the narrow strips were incubated with the alkaline phosphatase substrate BCIP-NBT (KPL, Gaithersburg, Md., USA) for 30 min., and then washed in distilled water and dried.

Panel of Sera Tested

The human sera were collected from clinically well-defined, typical LB patients corresponding to the various stages of LB (22 with erythema migrans [EM], 5 with carditis, 20 with neuroborreliosis [NB], 20 with Lyme arthritis [LA], 20 with acrodermatitis chronica atrophicans [ACA] and 10 with lymphadenosis cutis benigna [LCB]). Anti-Lyme IgGs were found by immunoblot, described previously and using whole cell lysates [4], in the sera of patients with LA, ACA and carditis. EM, NB and LCB were identified clinically, but not all the corresponding sera were found to be positive by in-house immunoblot [4], or using the commercially available kits (Vidas® Lyme (biomérieux), *Borrelia* IgG (Diasorin®) and *Borrelia* IgM (r-biopharm®)). On the other hand, all the cases of NB included in the study had detectable antibodies in the cerebrospinal fluid [CSF] (index extending from 2 to 27.1 with Vidas® Lyme (biomérieux)). The presence of IgM was sought only in the stage I and stage II clinical cases and not in the chronic stages.

The negative control group consisted of 31 sera previously found to be negative for the presence of anti-Lyme antibodies in conventional assays. Furthermore, 64 sera from healthy blood donors residing in a region endemic for Lyme disease (Monthley, Valais, Switzerland) were tested with the recombinant protein.

The strength of the reaction was evaluated as follows: [+], [++], [+++], [−] or equivocal results. The equivocal results were considered to be negative.

The results are given in table 4.

TABLE 4

Reactivity in Line immunoblot of human sera from patients with Lyme borreliosis, with 3 chimeric recombinant proteins bLYM114 (SEQ ID NO: 9), bLYM120 (SEQ ID NO: 11) and bLYM121 (SEQ ID NO: 14)

|  | IgG | | | | | | IgM | | |
|---|---|---|---|---|---|---|---|---|---|
|  | Stage I | Stage II | | Stage III | | | Stage I | Stage II | |
| Protein | EM (n = 22) | NB (n = 20) | Carditis (n = 5) | LA (n = 19) | ACA (n = 20) | LCB (n = 10) | EM (n = 22) | NB (n = 20) | Carditis (n = 5) |
| bLYM114 | 5 | 10 | 0 | 7 | 12 | 2 | 7 | 7 | 2 |
| bLYM120 | 6 | 7 | 0 | 8 | 6 | 0 | 11 | 7 | 2 |
| bLYM121 | 2 | 10 | 5 | 9 | 8 | 0 | 7 | 7 | 2 |
| Σ bLYM 114 + 120 + 121 | 9 | 13 | 5 | 18 | 17 | 2 | 11 | 7 | 2 |
| Positive sera (%) | 40.9% | 59.1% | 100% | 94.7% | 85% | 20% | 50% | 35% | 40% |
| and reaction strength | 1 [+++] 4 [++] 4 [+] | 8 [+++] 2 [++] 3 [+] | 4 [+++] 1 [+] | 7 [+++] 8 [++] 3 [+] | 8 [+++] 5 [++] 4 [+] | 1 [++] 1 [+] | 1 [+++] 7 [++] 5 [+] | 5 [++] 2 [+] | 2 [++] |
| Total positives and reaction strength |  | 66.7% 28 [+++] 20 [++] 16 [+] | | | | |  | 42.5% 1 [+++] 14 [++] 7 [+] | |

The specificity is 100% on the basis of 31 sera originating from healthy individuals determined to be Lyme-negative using the standard commercially available tests.

IgGs Detection

The results indicate that the recombinant chimeric fusion proteins are diagnostic tools that are sensitive at all stages of the infection for IgGs and IgMs. They demonstrate an additional effect of the three recombinant proteins based, respectively, on sequences of *Borrelia afzelii, B.* sensu stricto and *B. garinii* for the detection of IgGs. The combined use of the three chimeric recombinant proteins makes it possible, at stage I of the infection, to detect IgGs in 9 cases of patients with EM out of 22 (i.e. 40.9% sensitivity).

IgM Detection

Anti-chimera protein IgMs are found in 11 cases out of 22 (i.e. 50% sensitivity). These chimera proteins therefore detect the IgMs more often than the IgGs in the sera of stage-I LB patients. The tests performed as a control: in-house immunoblot [4], and the commercially available kit Borrelia IgM (r-biopharm®) do not further detect IgM-positive sera. In addition, 3 sera found to be negative using the immunoblot test and *Borrelia* IgM (r-biopharm®) are detected by the three chimeric proteins cited as example (3/3) or by one of the three proteins cited as example (1/3). The combined use of the three recombinant proteins makes it possible to improve the IgM detection sensitivity by 13.6% in stage I of the infection.

Example 4

Preparation of Plasmid Constructs Encoding the VlsE Chimeric Recombinant Proteins The DNA sequences encoding the various sequences of the protein are identified in table 5.

TABLE 5

|  | Sequence origin | | |
|---|---|---|---|
|  | *B. burgdorferi* species | | |
| protein | *B. sensu stricto* | *B. afzelii* | *B. garinii* |
| VlsE | — | — | *PBi ; **aa 20-293; ***AJ630106 (GenScript Corp) |
| IR6 | *B31; **aa 274-305; ***U76405 (GeneArt GmbH) | *ACA-1; **aa 172-188; ***U76405 (GeneArt GmbH) | *Ip90; **aa 167-191; ***AAN87834 (GeneArt GmbH) |

*Isolate;
**amino acids (aa);
***GenBank accession No.

The sequences were optimized for their expression in *E. coli* using GeneOptimize™ and synthesized respectively by GenScript corporation (Scotch Plains, N.J., USA) or GeneArt GmbH (Regensburg, Germany).

Additional modifications to the DNA, deletions or combinations of various sequences were carried out by PCR by genetic engineering using the PCR techniques well known to those skilled in the art and described, for example, in Sambrook J. et al., Molecular Cloning: A Laboratory Manual, 1989. The DNA sequences were ligated into the pMR [2] or pET-3d (Novagen®) expression vector. The plasmid constructs and the corresponding proteins cited as example (bLYM110, bLYM125) are described in table 6.

TABLE 6

Plasmid constructs and corresponding proteins

| | Recombinant protein characteristics | | Plasmid construct characteristics | |
|---|---|---|---|---|
| Name | N-terminal Tag | B. burgdorferi sequence | Parental vector | Site of insertion of the insert sequence into the vector |
| bLYM110 SEQ ID NO: 39 | 6 x His | VlsE garinii pBi aa 20-293 + 3 IR6 [sensu stricto B21 aa 274-305 + afzelii ACA-1aa 172-188 + garinii Ip90 aa 167-191] | pMR78 | 5'BamHI/ 3'HindIII |
| bLYM125 SEQ ID NO: 41 | 8 x His | | pET-3d | 5'NcoI/ 3'BamHI |

Example 5

Expression of the Recombinant Proteins of Example 4 and Purification

A plasmid construct described in example 4 was used to transform an *E. coli* bacterium (strain BL21) according to a conventional protocol known to those skilled in the art. The transformed bacteria were selected by virtue of their ampicillin resistance carried by the pMR or pET vector.

A clone of a recombinant bacterium was then selected in order to inoculate a preculture of 40 ml of 2×YT medium (16 g/l tryptone; 10 g/l yeast extract; 5 g/l NaCl, pH 7.0) containing 100 µg/ml ampicillin. After 15 to 18 hours of incubation at 30° C. with shaking at 250 rpm, this preculture was used to inoculate 1 liter of 2×YT medium containing 2% glucose and 100 µg/ml ampicillin. This culture was incubated at 30° C. with shaking at 250 rpm until the OD at 600 nm reaches 1.0/1.2. The culture was maintained for 3 hours 30 min. or 4 hours at 30° C. while adding 0.4 mM isopropyl-β-D-thio-galactopyranoside (IPTG) and harvested by centrifugation at 6000 g for 30 min. The cell pellet was stored at −60° C. For the purification, the wet biomass was resuspended in a lysis buffer containing protease inhibitors without EDTA (Roche) and benzonase nuclease (Novagen®), and subjected to cell rupture at 1.6 kBar in a cell disrupter (Constant Systems Ltd, Daventry, United Kingdom). The lysate was then centrifuged at 10 000 rpm for 45 minutes at 2-8° C. After filtration through a 0.22 µm filter, the supernatant was loaded onto an Ni-NTA column (Qiagen®) equilibrated in a lysis buffer. The resin was then washed with the same buffer until the $A_{280\ nm}$ reached the base line. An elution was carried out with the elution buffer, and the purified protein was dialyzed in a Pierce Slide-A-Lyser® 10000 or 20000 MWCO dialysis cassette against the dialysis buffer. The conditions for purification on Ni-NTA gel are described in table 7.

TABLE 7

Recombinant protein purification

| Protein | bLYM110 SEQ ID NO: 39 | bLYM125 SEQ ID NO: 41 |
|---|---|---|
| Lysis and washing buffer | Buffer A [1] | Buffer A [1] + 2M urea |
| Elution buffer | Buffer B [2] | Buffer B [2] modified with 600 mM imidazole |
| Elution step 1 | 86% Buffer A + 14% Buffer B (4CV) | 92% Buffer A + 8% Buffer B (4CV) |
| Elution step 2 | 100% Buffer B | 100% Buffer B |
| Purification yield mg protein/g wet biomass | 0.5 | 0.8 |
| Purification yield mg protein/L of culture | 8.7 | 17 |

[1] 50 mM sodium phosphate, 30 mM imidazole, 500 mM NaCl, 0.1% TWEEN 20, 5% glycerol, pH = 7.8
[2] 50 mM sodium phosphate, 325 mM imidazole, 500 mM NaCl, 5% glycerol, pH = 7.5

The samples were analyzed on NuPAG® Novex® 4-12% in a NuPAGE® MES-SDS circulating buffer, according to the instructions of the producer (Invitrogen™). The proteins were either stained with COOMASSIE BRILLIANT BLUE or were transferred electrophoretically onto a nitrocellulose membrane. The membrane was blocked with 5% (w/v) dry milk in PBS and incubated with an anti-pentahistidine antibody (Qiagen®) in PBS containing 0.05% TWEEN 20. A horseradish peroxidase-labeled goat anti-mouse IgG conjugate (Jackson Immunoresearch laboratories) in PBS/TWEEN was used as secondary antibody.

The protein concentration was determined using the Bradford Assay Kit (PIERCE COOMASSIE PLUS, Perbio Science) with BSA as protein standard.

Example 6

Detection of Human IgGs and IgMs with the Chimeric Recombinant Protein bLYM110 of Example 5 Using a Line Immunoblot Technique The recombinant protein was deposited onto a polyvinylidene difluoride membrane (PVDF, Immobilon, Millipore®, Bedford, Mass. USA) according to the following protocol: The protein concentration was adjusted to 1 mg/ml in PBS, pH 7.2, and diluted in PBS, pH 7.2, supplemented with 0.03% TWEEN 20 (dilution 1/200th). The PVDF membrane was wetted in methanol, washed in demineralized water and laid out on a wet blotting paper. A plastic ruler was immersed in the protein dilution and attached to the PVDF membrane. After depositing of the proteins and drying of the membranes, the membranes were cut vertically into narrow strips. Before use, the narrow strips were incubated with 5% gelatin in TBS, pH 7.5, for 1 hour at 37° C. The immunoblot protocols were carried out at ambient temperature as described by Bretz A. G. et al. [3]. The narrow strips were incubated for 2 hours with human sera diluted to 1/200th in TBS with 1% gelatin, washed and incubated with anti-human IgGs or IgMs labeled with alkaline phosphatase (Sigma™, St-Louis, USA) diluted to 1/1000th in TBS with 1% gelatin. After washing, the narrow strips were incubated with the BCIP-NBT substrate (KPL, Gaithersburg, Md., USA) for 30 minutes, washed in distilled water and dried.

Panel of Sera Tested

The human sera were collected from clinically well-defined, typical LB patients corresponding to the various stages of LB (22 with erythema migrans [EM], 5 with carditis, 20 with neuroborreliosis [NB], 20 with Lyme arthritis [LA], 20 with acrodermatitis chronica atrophicans [ACA] and 10 with lymphadenosis cutis benigna [LCB]). Anti-Lyme IgGs were found by immunoblot, described previously using whole cell lysates [4], in the sera of patients with LA, ACA and carditis. EM, NB and LCB were identified clinically, but not all the corresponding sera were found to be positive using the immunoblot [4], or using the commercially available kits (Vidas® Lyme (bioMérieux®), *Borrelia* IgG (Diasorin®) and *Borrelia* IgM (r-biopharm®)). On the other hand, all the cases of NB included in the study had detectable antibodies in the cerebrospinal fluid [CSF] (index extending from 2 to 27.1).

The negative control group consisted of 31 sera previously found to be negative for the presence of anti-Lyme antibodies in conventional assays. Furthermore, 64 sera from healthy blood donors residing in a region endemic for Lyme disease (Monthley, Valis, Switzerland) were tested with the recombinant protein. The strength of the reaction was evaluated as follows: [+] , [++], [+++], [−] or equivocal results. The equivocal results were considered to be negative.

The results are given in table 8 below.

TABLE 8

| IgG | | | | | | |
|---|---|---|---|---|---|---|
| Stage I | Stage II | | Stage III | | | Donors |
| EM (n = 22) | NB (n = 20) | Carditis (n = 5) | LA (n = 19) | ACA (n = 20) | Lymph. (n = 10) | (n = 64) |
| 17 | 20 | 5 | 19 | 20 | 9 | 6 |
| 77.3% | 100% | 100% | 100% | 100% | 90% | 9.4% |
| 12 [+++] | 11 [+++] | 4 [+++] | 13 [+++] | 20 [+++] | 3 [+++] | 6 [+] |
| 4 [++] | 7 [++] | 1 [++] | 4 [++] | | 2 [++] | |
| 1 [+] | 2 [+] | | 2 [+] | | 4 [+] | |
| Total IgG positives 93.7% | | | | | | |

| IgM | | | | | | |
|---|---|---|---|---|---|---|
| EM (n = 22) | NB (n = 20) | Carditis (n = 5) | | | | (n = 64) |
| 5 | 4 | 2 | | | | 1 |
| 22% | 20% | 40% | | | | 1.5% |
| 1 [++] | 2 [++] | 1 [++] | | | | 1 [+] |
| 4 [+] | 1 [+] | 1 [+] | | | | |
| Total IgM positives 23.4% | | | | | | |

IgG Detection

The results indicate that the recombinant protein bLYM110 is a diagnostic antigen that is highly sensitive at all stages of the infection for IgGs. At stage I of the infection, the IgGs were detected in 17 cases of patients with EM out of 22 (i.e. 77.3% sensitivity). Five of the patients with EM who are found to be negative with the recombinant protein are also found to be negative with the in-house immunoblot and with the commercially available kits. Seven EM sera found to be positive with the recombinant protein were not detected by immunoblot, which represents a 31.8% improvement in sensitivity with the recombinant protein. At the primary stage of the infection, in the absence of characteristic redness, the diagnosis can be difficult since the other clinical manifestations of Lyme disease are not specific. Furthermore, only a few patients with EM are detected using the conventional tests. Therefore, the protein of the invention improves the detection of IgGs at stage I of the infection, bringing their detection to more than 77% in patients with EM.

IgM Detection

Anti-chimera protein IgMs are found in 23.4% of the LB sera. The protein detects the IgGs more often than the IgMs in the sera of stage-I and -II LB patients.

Example 7

Evaluation and Validation of the Chimeric Recombinant Proteins bLYM114, bLYM120, bLYM121 and bLYM125 in a VIDAS® Test (bioMérieux)

This validation is carried out in a VIDAS® test using:
1) the chimeric recombinant proteins bLYM114, bLYM120 and bLYM121, obtained according to examples 1 and 2, for the IgM detection, and
2) the chimeric recombinant proteins bLYM114 and bLYM120, obtained according to examples 1 and 2, and the chimeric protein bLYM125, obtained according to examples 4 and 5, for the IgG detection.

The principle of the VIDAS® test is the following: a tip constitutes the solid support which also serves as a pipetting system for the reagents present in the strip. The recombinant protein(s) is (are) attached to the tip. After a dilution step, the sample is drawn up and forced back several times in the tip. This allows the anti-Lyme immunoglobulins in the sample to bind to the recombinant proteins. The unbound proteins are removed by washing. An anti-human-immunoglobulin antibody conjugated to alkaline phosphatase (ALP) is incubated in the tip, where it binds to the anti-Lyme immunoglobulins. Washing steps remove the unbound conjugate. During the final visualizing step, the alkaline phosphatase (ALP) substrate, 4-methylumbelliferyl phosphate, is hydrolyzed to 4-methyl-umbelliferone, the fluorescence of which emitted at 450 nm is measured. The intensity of the fluorescence is measured by means of the Vidas® optical system and is proportional to the presence of anti-Lyme immunoglobulins present in the sample. The results are analyzed automatically by the VIDAS® and expressed as RFV (Relative Fluorescent Value).

255 positive sera (equivocal sera+positive sera) and 298 negative sera (equivocal+negative) were thus assayed with the Vidas® system.

The Vidas® Lyme IgG tips are sensitized with 300 μL of solution comprising the bLYM114, bLYM120 and bLYM125 proteins of the invention, each at a concentration of 1 μg/mL in a common sensitizing solution.

In the first step, the sera are incubated for 5.3 min. for the formation of the antigen-antibody complexes. In the second step, anti-human-IgGs labeled with ALP are incubated for 5.3 min.

The results are given as an index relative to a positivity threshold positioned at 135 RFV in the protocol.

Among the 255 positive sera tested, 246 are positive and 9 are falsely negative, which corresponds to a sensitivity of 96.5%.

Among the 298 negative sera tested, 284 are negative and 14 are falsely positive, which corresponds to a specificity of 95.3%.

LITERATURE REFERENCES

1. Göttner G. et al., Int. J. Microbiol. 293, Suppl. 37, 172-173 (2004)
2. Arnaud N. et al., Gene 1997; 199:149-156.
3. Bretz A. G., K. Ryffel, P. Hutter, E. Dayer and O. Péter. Specificities and sensitivities of four monoclonal antibodies for typing of *Borrelia burgdorferi* sensu lato isolates. Clin. Diag. Lab. Immunol. 2001; 8: 376-384.
4. Ryffel K., Péter O., Rutti B. and E. Dayer. Scored antibody reactivity by immunoblot suggests organotropism of *Borrelia burgdorferi* sensu stricto, *B. garinii, B. afzelii* and *B. valaisiana* in human. J. Clin. Microbial. 1999; 37:4086-92

The invention claimed is:

1. A polypeptide comprising an amino acid sequence selected from the group consisting of the amino acid sequences of SEQ ID NOs: 8-14.

2. A diagnostic kit comprising the polypeptide as claimed in claim 1.

3. The diagnostic kit as claimed in claim 2, further comprising an anti-human-immunoglobulin labeled with a label.

4. The diagnostic kit as claimed in claim 2, wherein the polypeptide is immobilized on a solid support.

5. The diagnostic kit as claimed in claim 2, comprising (i) a first polypeptide comprising the amino acid sequence of SEQ ID NO: 9, (ii) a second polypeptide comprising the amino acid sequence of SEQ ID NO: 11, and (iii) a third polypeptide comprising the amino acid sequence of SEQ ID NO: 14.

6. The polypeptide as claimed in claim 1, comprising the amino acid sequence of SEQ ID NO: 8.

7. A diagnostic kit comprising the polypeptide as claimed in claim 6 and an anti-human-immunoglobulin labeled with a label.

8. The polypeptide as claimed in claim 1, comprising the amino acid sequence of SEQ ID NO: 9.

9. A diagnostic kit comprising the polypeptide as claimed in claim 8 and an anti-human-immunoglobulin labeled with a label.

10. The polypeptide as claimed in claim 1, comprising the amino acid sequence of SEQ ID NO: 10.

11. A diagnostic kit comprising the polypeptide as claimed in claim 10 and an anti-human-immunoglobulin labeled with a label.

12. The polypeptide as claimed in claim 1, comprising the amino acid sequence of SEQ ID NO: 11.

13. A diagnostic kit comprising the polypeptide as claimed in claim 12 and an anti-human-immunoglobulin labeled with a label.

14. The polypeptide as claimed in claim 1, comprising the amino acid sequence of SEQ ID NO: 12.

15. A diagnostic kit comprising the polypeptide as claimed in claim 14 and an anti-human-immunoglobulin labeled with a label.

16. The polypeptide as claimed in claim 1, comprising the amino acid sequence of SEQ ID NO: 13.

17. A diagnostic kit comprising the polypeptide as claimed in claim 16 and an anti-human-immunoglobulin labeled with a label.

18. The polypeptide as claimed in claim 1, comprising the amino acid sequence of SEQ ID NO: 14.

19. A diagnostic kit comprising the polypeptide as claimed in claim 18 and an anti-human-immunoglobulin labeled with a label.

20. A method for the in vitro diagnosis of Lyme borreliosis using a biological sample, comprising:
bringing the biological sample into contact with at least one polypeptide as claimed in claim 1; and
determining whether there is formation of an immunological complex between the polypeptide and antibodies of the biological sample.

21. The method as claimed in claim 20, wherein the antibodies of the biological sample are IgGs and/or IgMs.

22. The method as claimed in claim 21, wherein the formation of the immunological complex is determined by adding at least one anti-human-immunoglobulin labeled with a label.

23. The method as claimed in claim 20, wherein the polypeptide is immobilized on a solid support.

24. The method as claimed in claim 21, wherein the polypeptide is immobilized on a solid support.

25. The method as claimed in claim 22, wherein the polypeptide is immobilized on a solid support.

* * * * *

SEQUENCE LISTING

<160> NUMBER OF SEQ ID NOS: 43

<210> SEQ ID NO 1
<211> LENGTH: 149
<212> TYPE: PRT
<213> ORGANISM: Borrelia sp.

<400> SEQUENCE: 1

```
Ser Leu Thr Gly Lys Ala Arg Leu Glu Ser Ser Val Lys Asp Ile Thr
1               5                   10                  15

Asn Glu Ile Glu Lys Ala Ile Lys Glu Ala Glu Asp Ala Gly Val Lys
            20                  25                  30

Thr Asp Ala Phe Thr Glu Thr Gln Thr Gly Gly Lys Val Ala Gly Pro
        35                  40                  45

Lys Ile Arg Ala Ala Lys Ile Arg Val Ala Asp Leu Thr Ile Lys Phe
    50                  55                  60

Leu Glu Ala Thr Glu Glu Glu Thr Ile Thr Phe Lys Glu Asn Gly Ala
65                  70                  75                  80

Gly Glu Asp Glu Phe Ser Gly Ile Tyr Asp Leu Ile Leu Asn Ala Ala
                85                  90                  95

Lys Ala Val Glu Lys Ile Gly Met Lys Asp Met Thr Lys Thr Val Glu
            100                 105                 110

Glu Ala Ala Lys Glu Asn Pro Lys Thr Thr Ala Asn Gly Ile Ile Glu
        115                 120                 125

Ile Val Lys Val Met Lys Ala Lys Val Glu Asn Ile Lys Glu Lys Gln
    130                 135                 140

Thr Lys Asn Gln Lys
145
```

<210> SEQ ID NO 2
<211> LENGTH: 211
<212> TYPE: PRT
<213> ORGANISM: Borrelia sp.

<400> SEQUENCE: 2

```
Lys Lys Asn Thr Leu Ser Ala Ile Leu Met Thr Leu Phe Leu Phe Ile
1               5                   10                  15

Ser Cys Asn Asn Ser Gly Lys Gly Gly Asp Ser Ala Ser Thr Asn Pro
            20                  25                  30

Ala Asp Glu Ser Ala Lys Gly Pro Asn Leu Thr Glu Ile Ser Lys Lys
        35                  40                  45

Ile Thr Asp Ser Asn Ala Phe Val Leu Ala Val Lys Glu Val Glu Thr
    50                  55                  60

Leu Val Leu Ser Ile Asp Glu Leu Ala Lys Lys Ala Ile Gly Gln Lys
65                  70                  75                  80

Ile Asp Asn Asn Asn Gly Leu Ala Ala Leu Asn Asn Gln Asn Gly Ser
                85                  90                  95

Leu Leu Ala Gly Ala Tyr Ala Ile Ser Thr Leu Ile Thr Glu Lys Leu
            100                 105                 110

Ser Lys Leu Lys Asn Leu Glu Glu Leu Lys Thr Glu Ile Ala Lys Ala
        115                 120                 125

Lys Lys Cys Ser Glu Glu Phe Thr Asn Lys Leu Lys Ser Gly His Ala
    130                 135                 140

Asp Leu Gly Lys Gln Asp Ala Thr Asp Asp His Ala Lys Ala Ala Ile
145                 150                 155                 160

Leu Lys Thr His Ala Thr Thr Asp Lys Gly Ala Lys Glu Phe Lys Asp
```

-continued

```
                    165                 170                 175

Leu Phe Glu Ser Val Glu Gly Leu Leu Lys Ala Ala Gln Val Ala Leu
                180                 185                 190

Thr Asn Ser Val Lys Glu Leu Thr Ser Pro Val Val Ala Glu Ser Pro
            195                 200                 205

Lys Lys Pro
    210

<210> SEQ ID NO 3
<211> LENGTH: 164
<212> TYPE: PRT
<213> ORGANISM: Borrelia sp.

<400> SEQUENCE: 3

Thr Gly Ala Thr Lys Ile Arg Leu Glu Arg Ser Ala Lys Asp Ile Thr
1               5                   10                  15

Asp Glu Ile Asp Ala Ile Lys Lys Asp Ala Ala Leu Lys Gly Val Asn
            20                  25                  30

Phe Asp Ala Phe Lys Asp Lys Thr Gly Ser Gly Val Ser Glu Asn
        35                  40                  45

Pro Phe Ile Leu Glu Ala Lys Val Arg Ala Thr Thr Val Ala Glu Lys
    50                  55                  60

Phe Val Ile Ala Ile Glu Glu Ala Thr Lys Leu Lys Glu Thr Gly
65                  70                  75                  80

Ser Ser Gly Glu Phe Ser Ala Met Tyr Asp Leu Met Phe Glu Val Ser
                85                  90                  95

Lys Pro Leu Gln Lys Leu Gly Ile Gln Glu Met Thr Lys Thr Val Ser
            100                 105                 110

Asp Ala Ala Glu Glu Asn Pro Pro Thr Thr Ala Gln Gly Val Leu Glu
        115                 120                 125

Ile Ala Lys Lys Met Arg Glu Lys Leu Gln Arg Val His Thr Lys Asn
    130                 135                 140

Tyr Cys Thr Leu Lys Lys Lys Glu Asn Ser Thr Phe Thr Asp Glu Lys
145                 150                 155                 160

Cys Lys Asn Asn

<210> SEQ ID NO 4
<211> LENGTH: 185
<212> TYPE: PRT
<213> ORGANISM: Borrelia sp.

<400> SEQUENCE: 4

Asn Thr Ser Ala Asn Ser Ala Asp Glu Ser Val Lys Gly Pro Asn Leu
1               5                   10                  15

Thr Glu Ile Ser Lys Lys Ile Thr Asp Ser Asn Ala Val Leu Leu Ala
            20                  25                  30

Val Lys Glu Val Glu Ala Leu Leu Ser Ser Ile Asp Glu Ile Ala Ala
        35                  40                  45

Lys Ala Ile Gly Lys Lys Ile His Gln Asn Asn Gly Leu Asp Thr Glu
    50                  55                  60

Asn Asn His Asn Gly Ser Leu Leu Ala Gly Ala Tyr Ala Ile Ser Thr
65                  70                  75                  80

Leu Ile Lys Gln Lys Leu Asp Gly Leu Lys Asn Glu Gly Leu Lys Glu
                85                  90                  95

Lys Ile Asp Ala Ala Lys Lys Cys Ser Glu Thr Phe Thr Asn Lys Leu
            100                 105                 110
```

```
Lys Glu Lys His Thr Asp Ser Phe Gly Lys Glu Gly Val Thr Asp Ala
            115                 120                 125

Asp Ala Lys Glu Ala Ile Leu Lys Thr Asn Gly Thr Lys Thr Lys Gly
        130                 135                 140

Ala Glu Glu Leu Gly Lys Leu Phe Glu Ser Val Glu Val Leu Ser Lys
145                 150                 155                 160

Ala Ala Lys Glu Met Leu Ala Asn Ser Val Lys Glu Leu Thr Ser Pro
                165                 170                 175

Val Val Ala Glu Ser Pro Lys Lys Pro
                180                 185

<210> SEQ ID NO 5
<211> LENGTH: 162
<212> TYPE: PRT
<213> ORGANISM: Borrelia sp.

<400> SEQUENCE: 5

Thr Gly Glu Thr Lys Ile Arg Leu Glu Ser Ala Gln Glu Ile Lys
1               5                   10                  15

Asp Glu Ile Asn Lys Ile Lys Ala Asn Ala Lys Lys Glu Gly Val Lys
                20                  25                  30

Phe Glu Ala Phe Thr Asp Lys Gln Thr Gly Ser Lys Val Ser Glu Lys
            35                  40                  45

Pro Glu Phe Ile Leu Lys Ala Lys Ile Lys Ala Ile Gln Val Ala Glu
        50                  55                  60

Lys Phe Val Lys Ala Ile Lys Glu Glu Ala Glu Lys Leu Lys Lys Ser
65                  70                  75                  80

Gly Ser Ser Gly Ala Phe Ser Ala Met Tyr Asp Leu Met Leu Asp Val
                85                  90                  95

Ser Lys Pro Leu Glu Glu Ile Gly Ile Gln Lys Met Thr Gly Thr Val
                100                 105                 110

Thr Lys Glu Ala Glu Lys Thr Pro Pro Thr Thr Ala Glu Gly Ile Leu
            115                 120                 125

Ala Ile Ala Gln Ala Met Glu Glu Lys Leu Asn Asn Val Asn Lys Lys
        130                 135                 140

Gln Gln Asp Ala Leu Lys Asn Leu Glu Glu Lys Ala Asn Thr Ala Ala
145                 150                 155                 160

Thr Thr

<210> SEQ ID NO 6
<211> LENGTH: 154
<212> TYPE: PRT
<213> ORGANISM: Borrelia sp.

<400> SEQUENCE: 6

Ser Gly Thr Gly Lys Ala Arg Leu Glu Ser Val Lys Asp Ile Thr
1               5                   10                  15

Asp Glu Ile Asp Lys Ala Ile Lys Glu Ala Ile Ala Asp Gly Val Lys
                20                  25                  30

Leu Asn Glu Leu Glu Glu Asn Lys Thr Gly Ala Lys Lys Gly Gly Pro
            35                  40                  45

Gln Ile Arg Asp Ala Lys Ile Arg Val Ile Asn Leu Ser Val Lys Phe
        50                  55                  60

Leu Lys Glu Ile Glu Glu Glu Ala Asn Ile Leu Lys Asp Asn Val Gly
65                  70                  75                  80
```

```
Met Asn Lys Val Asp Lys Asp Gln Leu Leu Lys Asp Met Tyr Asp Leu
                85                  90                  95

Met Leu Asn Ala Ala Gly Ser Leu Gln Lys Leu Gly Leu Gln Glu Met
            100                 105                 110

Ile Lys Thr Val Thr Gln Ala Ala Glu Lys Thr Pro Pro Thr Thr Val
        115                 120                 125

Glu Gly Ile Leu Met Ile Ala Asn Thr Ile Glu Asp Lys Leu Lys Lys
    130                 135                 140

Ile Lys Gly Lys Gln Glu Thr Asn Lys Lys
145                 150
```

<210> SEQ ID NO 7
<211> LENGTH: 176
<212> TYPE: PRT
<213> ORGANISM: Borrelia sp.

<400> SEQUENCE: 7

```
Asp Glu Ser Ala Lys Gly Pro Asn Leu Thr Val Ile Ser Lys Lys Ile
1               5                   10                  15

Thr Asp Ser Asn Ala Phe Leu Leu Ala Val Lys Glu Val Glu Ala Leu
            20                  25                  30

Leu Ser Ser Ile Asp Glu Leu Ser Lys Ala Ile Gly Lys Lys Ile Lys
        35                  40                  45

Asn Asp Gly Thr Leu Asp Asn Glu Ala Asn Arg Asn Glu Ser Leu Ile
50                  55                  60

Ala Gly Ala Tyr Glu Ile Ser Lys Leu Ile Thr Gln Lys Leu Ser Val
65                  70                  75                  80

Leu Asn Ser Glu Glu Leu Lys Glu Lys Ile Lys Glu Ala Lys Asp Cys
                85                  90                  95

Ser Glu Lys Phe Thr Thr Lys Leu Lys Asp Ser His Ala Glu Leu Gly
            100                 105                 110

Ile Gln Ser Val Gln Asp Asn Ala Lys Lys Ala Ile Leu Lys Thr
        115                 120                 125

His Gly Thr Lys Asp Lys Gly Ala Lys Glu Leu Glu Glu Leu Phe Lys
    130                 135                 140

Ser Leu Glu Ser Leu Ser Lys Ala Ala Gln Ala Ala Leu Thr Asn Ser
145                 150                 155                 160

Val Lys Glu Leu Thr Asn Pro Val Ala Glu Ser Pro Lys Lys Pro
                165                 170                 175
```

<210> SEQ ID NO 8
<211> LENGTH: 361
<212> TYPE: PRT
<213> ORGANISM: Borrelia sp.

<400> SEQUENCE: 8

```
Met Ser Leu Thr Gly Lys Ala Arg Leu Glu Ser Ser Val Lys Asp Ile
1               5                   10                  15

Thr Asn Glu Ile Glu Lys Ala Ile Lys Glu Ala Glu Asp Ala Gly Val
            20                  25                  30

Lys Thr Asp Ala Phe Thr Glu Thr Gln Thr Gly Gly Lys Val Ala Gly
        35                  40                  45

Pro Lys Ile Arg Ala Ala Lys Ile Arg Val Ala Asp Leu Thr Ile Lys
    50                  55                  60

Phe Leu Glu Ala Thr Glu Glu Glu Thr Ile Thr Phe Lys Glu Asn Gly
65                  70                  75                  80
```

```
Ala Gly Glu Asp Glu Phe Ser Gly Ile Tyr Asp Leu Ile Leu Asn Ala
                85                  90                  95

Ala Lys Ala Val Glu Lys Ile Gly Met Lys Asp Met Thr Lys Thr Val
            100                 105                 110

Glu Glu Ala Ala Lys Glu Asn Pro Lys Thr Thr Ala Asn Gly Ile Ile
        115                 120                 125

Glu Ile Val Lys Val Met Lys Ala Lys Val Glu Asn Ile Lys Glu Lys
    130                 135                 140

Gln Thr Lys Asn Gln Lys Lys Asn Thr Leu Ser Ala Ile Leu Met
145                 150                 155                 160

Thr Leu Phe Leu Phe Ile Ser Cys Asn Asn Ser Gly Lys Gly Gly Asp
                165                 170                 175

Ser Ala Ser Thr Asn Pro Ala Asp Glu Ser Ala Lys Gly Pro Asn Leu
            180                 185                 190

Thr Glu Ile Ser Lys Lys Ile Thr Asp Ser Asn Ala Phe Val Leu Ala
        195                 200                 205

Val Lys Glu Val Glu Thr Leu Val Leu Ser Ile Asp Glu Leu Ala Lys
    210                 215                 220

Lys Ala Ile Gly Gln Lys Ile Asp Asn Asn Gly Leu Ala Ala Leu
225                 230                 235                 240

Asn Asn Gln Asn Gly Ser Leu Leu Ala Gly Ala Tyr Ala Ile Ser Thr
                245                 250                 255

Leu Ile Thr Glu Lys Leu Ser Lys Leu Lys Asn Leu Glu Glu Leu Lys
            260                 265                 270

Thr Glu Ile Ala Lys Ala Lys Lys Cys Ser Glu Glu Phe Thr Asn Lys
        275                 280                 285

Leu Lys Ser Gly His Ala Asp Leu Gly Lys Gln Asp Ala Thr Asp Asp
    290                 295                 300

His Ala Lys Ala Ala Ile Leu Lys Thr His Ala Thr Thr Asp Lys Gly
305                 310                 315                 320

Ala Lys Glu Phe Lys Asp Leu Phe Glu Ser Val Glu Gly Leu Leu Lys
                325                 330                 335

Ala Ala Gln Val Ala Leu Thr Asn Ser Val Lys Glu Leu Thr Ser Pro
            340                 345                 350

Val Val Ala Glu Ser Pro Lys Lys Pro
        355                 360

<210> SEQ ID NO 9
<211> LENGTH: 370
<212> TYPE: PRT
<213> ORGANISM: Borrelia sp.

<400> SEQUENCE: 9

Met Arg Gly Ser His His His His His His Ser Leu Thr Gly Lys Ala
1               5                   10                  15

Arg Leu Glu Ser Ser Val Lys Asp Ile Thr Asn Glu Ile Glu Lys Ala
            20                  25                  30

Ile Lys Glu Ala Glu Asp Ala Gly Val Lys Thr Asp Ala Phe Thr Glu
        35                  40                  45

Thr Gln Thr Gly Gly Lys Val Ala Gly Pro Lys Ile Arg Ala Ala Lys
    50                  55                  60

Ile Arg Val Ala Asp Leu Thr Ile Lys Phe Leu Glu Ala Thr Glu Glu
65                  70                  75                  80

Glu Thr Ile Thr Phe Lys Glu Asn Gly Ala Gly Glu Asp Glu Phe Ser
                85                  90                  95
```

```
Gly Ile Tyr Asp Leu Ile Leu Asn Ala Ala Lys Ala Val Glu Lys Ile
                100                 105                 110

Gly Met Lys Asp Met Thr Lys Thr Val Glu Glu Ala Ala Lys Glu Asn
            115                 120                 125

Pro Lys Thr Thr Ala Asn Gly Ile Ile Glu Ile Val Lys Val Met Lys
    130                 135                 140

Ala Lys Val Glu Asn Ile Lys Glu Lys Gln Thr Lys Asn Gln Lys Lys
145                 150                 155                 160

Lys Asn Thr Leu Ser Ala Ile Leu Met Thr Leu Phe Leu Phe Ile Ser
                165                 170                 175

Cys Asn Asn Ser Gly Lys Gly Gly Asp Ser Ala Ser Thr Asn Pro Ala
            180                 185                 190

Asp Glu Ser Ala Lys Gly Pro Asn Leu Thr Glu Ile Ser Lys Lys Ile
    195                 200                 205

Thr Asp Ser Asn Ala Phe Val Leu Ala Val Lys Glu Val Glu Thr Leu
210                 215                 220

Val Leu Ser Ile Asp Glu Leu Ala Lys Lys Ala Ile Gly Gln Lys Ile
225                 230                 235                 240

Asp Asn Asn Asn Gly Leu Ala Ala Leu Asn Asn Gln Asn Gly Ser Leu
                245                 250                 255

Leu Ala Gly Ala Tyr Ala Ile Ser Thr Leu Ile Thr Glu Lys Leu Ser
            260                 265                 270

Lys Leu Lys Asn Leu Glu Glu Leu Lys Thr Glu Ile Ala Lys Ala Lys
    275                 280                 285

Lys Cys Ser Glu Glu Phe Thr Asn Lys Leu Lys Ser Gly His Ala Asp
290                 295                 300

Leu Gly Lys Gln Asp Ala Thr Asp Asp His Ala Lys Ala Ala Ile Leu
305                 310                 315                 320

Lys Thr His Ala Thr Thr Asp Lys Gly Ala Lys Glu Phe Lys Asp Leu
                325                 330                 335

Phe Glu Ser Val Glu Gly Leu Leu Lys Ala Ala Gln Val Ala Leu Thr
            340                 345                 350

Asn Ser Val Lys Glu Leu Thr Ser Pro Val Val Ala Glu Ser Pro Lys
    355                 360                 365

Lys Pro
    370

<210> SEQ ID NO 10
<211> LENGTH: 350
<212> TYPE: PRT
<213> ORGANISM: Borrelia sp.

<400> SEQUENCE: 10

Met Thr Gly Ala Thr Lys Ile Arg Leu Glu Arg Ser Ala Lys Asp Ile
1               5                   10                  15

Thr Asp Glu Ile Asp Ala Ile Lys Lys Asp Ala Ala Leu Lys Gly Val
            20                  25                  30

Asn Phe Asp Ala Phe Lys Asp Lys Thr Gly Ser Gly Val Ser Glu
        35                  40                  45

Asn Pro Phe Ile Leu Glu Ala Lys Val Arg Ala Thr Thr Val Ala Glu
    50                  55                  60

Lys Phe Val Ile Ala Ile Glu Glu Ala Thr Lys Leu Lys Glu Thr
65                  70                  75                  80

Gly Ser Ser Gly Glu Phe Ser Ala Met Tyr Asp Leu Met Phe Glu Val
```

```
            85                  90                  95
Ser Lys Pro Leu Gln Lys Leu Gly Ile Gln Glu Met Thr Lys Thr Val
            100                 105                 110

Ser Asp Ala Ala Glu Glu Asn Pro Pro Thr Thr Ala Gln Gly Val Leu
            115                 120                 125

Glu Ile Ala Lys Lys Met Arg Glu Lys Leu Gln Arg Val His Thr Lys
        130                 135                 140

Asn Tyr Cys Thr Leu Lys Lys Glu Asn Ser Thr Phe Thr Asp Glu
145                 150                 155                 160

Lys Cys Lys Asn Asn Thr Ser Ala Asn Ser Ala Asp Glu Ser Val
                165                 170                 175

Lys Gly Pro Asn Leu Thr Glu Ile Ser Lys Lys Ile Thr Asp Ser Asn
                180                 185                 190

Ala Val Leu Leu Ala Val Lys Glu Val Glu Ala Leu Leu Ser Ser Ile
            195                 200                 205

Asp Glu Ile Ala Ala Lys Ala Ile Gly Lys Lys Ile His Gln Asn Asn
        210                 215                 220

Gly Leu Asp Thr Glu Asn Asn His Asn Gly Ser Leu Leu Ala Gly Ala
225                 230                 235                 240

Tyr Ala Ile Ser Thr Leu Ile Lys Gln Lys Leu Asp Gly Leu Lys Asn
                245                 250                 255

Glu Gly Leu Lys Glu Lys Ile Asp Ala Ala Lys Lys Cys Ser Glu Thr
            260                 265                 270

Phe Thr Asn Lys Leu Lys Glu Lys His Thr Asp Ser Phe Gly Lys Glu
        275                 280                 285

Gly Val Thr Asp Ala Asp Ala Lys Glu Ala Ile Leu Lys Thr Asn Gly
        290                 295                 300

Thr Lys Thr Lys Gly Ala Glu Glu Leu Gly Lys Leu Phe Glu Ser Val
305                 310                 315                 320

Glu Val Leu Ser Lys Ala Ala Lys Glu Met Leu Ala Asn Ser Val Lys
                325                 330                 335

Glu Leu Thr Ser Pro Val Val Ala Glu Ser Pro Lys Lys Pro
            340                 345                 350

<210> SEQ ID NO 11
<211> LENGTH: 359
<212> TYPE: PRT
<213> ORGANISM: Borrelia sp.

<400> SEQUENCE: 11

Met Arg Gly Ser His His His His His His Thr Gly Ala Thr Lys Ile
1               5                   10                  15

Arg Leu Glu Arg Ser Ala Lys Asp Ile Thr Asp Glu Ile Asp Ala Ile
            20                  25                  30

Lys Lys Asp Ala Ala Leu Lys Gly Val Asn Phe Asp Ala Phe Lys Asp
        35                  40                  45

Lys Lys Thr Gly Ser Gly Val Ser Glu Asn Pro Phe Ile Leu Glu Ala
    50                  55                  60

Lys Val Arg Ala Thr Thr Val Ala Glu Lys Phe Val Ile Ala Ile Glu
65                  70                  75                  80

Glu Glu Ala Thr Lys Leu Lys Glu Thr Gly Ser Ser Gly Glu Phe Ser
                85                  90                  95

Ala Met Tyr Asp Leu Met Phe Glu Val Ser Lys Pro Leu Gln Lys Leu
            100                 105                 110
```

```
Gly Ile Gln Glu Met Thr Lys Thr Val Ser Asp Ala Ala Glu Glu Asn
            115                 120                 125

Pro Pro Thr Thr Ala Gln Gly Val Leu Glu Ile Ala Lys Lys Met Arg
        130                 135                 140

Glu Lys Leu Gln Arg Val His Thr Lys Asn Tyr Cys Thr Leu Lys Lys
145                 150                 155                 160

Lys Glu Asn Ser Thr Phe Thr Asp Glu Lys Cys Lys Asn Asn Asn Thr
                165                 170                 175

Ser Ala Asn Ser Ala Asp Glu Ser Val Lys Gly Pro Asn Leu Thr Glu
            180                 185                 190

Ile Ser Lys Lys Ile Thr Asp Ser Asn Ala Val Leu Leu Ala Val Lys
        195                 200                 205

Glu Val Glu Ala Leu Leu Ser Ser Ile Asp Glu Ile Ala Ala Lys Ala
210                 215                 220

Ile Gly Lys Lys Ile His Gln Asn Asn Gly Leu Asp Thr Glu Asn Asn
225                 230                 235                 240

His Asn Gly Ser Leu Leu Ala Gly Ala Tyr Ala Ile Ser Thr Leu Ile
                245                 250                 255

Lys Gln Lys Leu Asp Gly Leu Lys Asn Glu Gly Leu Lys Glu Lys Ile
            260                 265                 270

Asp Ala Ala Lys Lys Cys Ser Glu Thr Phe Thr Asn Lys Leu Lys Glu
        275                 280                 285

Lys His Thr Asp Ser Phe Gly Lys Glu Gly Val Thr Asp Ala Asp Ala
    290                 295                 300

Lys Glu Ala Ile Leu Lys Thr Asn Gly Thr Lys Thr Lys Gly Ala Glu
305                 310                 315                 320

Glu Leu Gly Lys Leu Phe Glu Ser Val Glu Val Leu Ser Lys Ala Ala
                325                 330                 335

Lys Glu Met Leu Ala Asn Ser Val Lys Glu Leu Thr Ser Pro Val Val
            340                 345                 350

Ala Glu Ser Pro Lys Lys Pro
        355

<210> SEQ ID NO 12
<211> LENGTH: 493
<212> TYPE: PRT
<213> ORGANISM: Borrelia sp.

<400> SEQUENCE: 12

Met Thr Gly Glu Thr Lys Ile Arg Leu Glu Ser Ser Ala Gln Glu Ile
1               5                   10                  15

Lys Asp Glu Ile Asn Lys Ile Lys Ala Asn Ala Lys Lys Glu Gly Val
            20                  25                  30

Lys Phe Glu Ala Phe Thr Asp Lys Gln Thr Gly Ser Lys Val Ser Glu
        35                  40                  45

Lys Pro Glu Phe Ile Leu Lys Ala Lys Ile Lys Ala Ile Gln Val Ala
    50                  55                  60

Glu Lys Phe Val Lys Ala Ile Lys Glu Ala Glu Lys Leu Lys Lys
65                  70                  75                  80

Ser Gly Ser Ser Gly Ala Phe Ser Ala Met Tyr Asp Leu Met Leu Asp
                85                  90                  95

Val Ser Lys Pro Leu Glu Glu Ile Gly Ile Gln Lys Met Thr Gly Thr
            100                 105                 110

Val Thr Lys Glu Ala Glu Lys Thr Pro Pro Thr Thr Ala Glu Gly Ile
        115                 120                 125
```

```
Leu Ala Ile Ala Gln Ala Met Glu Glu Lys Leu Asn Val Asn Lys
            130                 135                 140

Lys Gln Gln Asp Ala Leu Lys Asn Leu Glu Glu Lys Ala Asn Thr Ala
145                 150                 155                 160

Ala Thr Thr Ser Gly Thr Gly Lys Ala Arg Leu Glu Ser Ser Val Lys
                165                 170                 175

Asp Ile Thr Asp Glu Ile Asp Lys Ala Ile Lys Glu Ala Ile Ala Asp
                180                 185                 190

Gly Val Lys Leu Asn Glu Leu Glu Glu Asn Lys Thr Gly Ala Lys Lys
                195                 200                 205

Gly Gly Pro Gln Ile Arg Asp Ala Lys Ile Arg Val Ile Asn Leu Ser
210                 215                 220

Val Lys Phe Leu Lys Glu Ile Glu Glu Ala Asn Ile Leu Lys Asp
225                 230                 235                 240

Asn Val Gly Met Asn Lys Val Asp Lys Asp Gln Leu Leu Lys Asp Met
                245                 250                 255

Tyr Asp Leu Met Leu Asn Ala Ala Gly Ser Leu Gln Lys Leu Gly Leu
                260                 265                 270

Gln Glu Met Ile Lys Thr Val Thr Gln Ala Ala Glu Lys Thr Pro Pro
                275                 280                 285

Thr Thr Val Glu Gly Ile Leu Met Ile Ala Asn Thr Ile Glu Asp Lys
290                 295                 300

Leu Lys Lys Ile Lys Gly Lys Gln Glu Thr Asn Lys Lys Asp Glu Ser
305                 310                 315                 320

Ala Lys Gly Pro Asn Leu Thr Val Ile Ser Lys Lys Ile Thr Asp Ser
                325                 330                 335

Asn Ala Phe Leu Leu Ala Val Lys Glu Val Glu Ala Leu Leu Ser Ser
                340                 345                 350

Ile Asp Glu Leu Ser Lys Ala Ile Gly Lys Lys Ile Lys Asn Asp Gly
                355                 360                 365

Thr Leu Asp Asn Glu Ala Asn Arg Asn Glu Ser Leu Ile Ala Gly Ala
                370                 375                 380

Tyr Glu Ile Ser Lys Leu Ile Thr Gln Lys Leu Ser Val Leu Asn Ser
385                 390                 395                 400

Glu Glu Leu Lys Glu Lys Ile Lys Glu Ala Lys Asp Cys Ser Glu Lys
                405                 410                 415

Phe Thr Thr Lys Leu Lys Asp Ser His Ala Glu Leu Gly Ile Gln Ser
                420                 425                 430

Val Gln Asp Asp Asn Ala Lys Lys Ala Ile Leu Lys Thr His Gly Thr
                435                 440                 445

Lys Asp Lys Gly Ala Lys Glu Leu Glu Glu Leu Phe Lys Ser Leu Glu
450                 455                 460

Ser Leu Ser Lys Ala Ala Gln Ala Ala Leu Thr Asn Ser Val Lys Glu
465                 470                 475                 480

Leu Thr Asn Pro Val Val Ala Glu Ser Pro Lys Lys Pro
                485                 490
```

<210> SEQ ID NO 13
<211> LENGTH: 502
<212> TYPE: PRT
<213> ORGANISM: Borrelia sp.

<400> SEQUENCE: 13

Met Arg Gly Ser His His His His His His Thr Gly Glu Thr Lys Ile

```
1               5                   10                  15
Arg Leu Glu Ser Ser Ala Gln Glu Ile Lys Asp Glu Ile Asn Lys Ile
                20                  25                  30
Lys Ala Asn Ala Lys Lys Glu Gly Val Lys Phe Glu Ala Phe Thr Asp
                35                  40                  45
Lys Gln Thr Gly Ser Lys Val Ser Glu Lys Pro Glu Phe Ile Leu Lys
                50                  55                  60
Ala Lys Ile Lys Ala Ile Gln Val Ala Glu Lys Phe Val Lys Ala Ile
65                      70                  75                  80
Lys Glu Glu Ala Glu Lys Leu Lys Lys Ser Gly Ser Ser Gly Ala Phe
                        85                  90                  95
Ser Ala Met Tyr Asp Leu Met Leu Asp Val Ser Lys Pro Leu Glu Glu
                100                 105                 110
Ile Gly Ile Gln Lys Met Thr Gly Thr Val Thr Lys Glu Ala Glu Lys
                115                 120                 125
Thr Pro Pro Thr Thr Ala Glu Gly Ile Leu Ala Ile Ala Gln Ala Met
                130                 135                 140
Glu Glu Lys Leu Asn Asn Val Asn Lys Lys Gln Gln Asp Ala Leu Lys
145                     150                 155                 160
Asn Leu Glu Glu Lys Ala Asn Thr Ala Ala Thr Thr Ser Gly Thr Gly
                        165                 170                 175
Lys Ala Arg Leu Glu Ser Ser Val Lys Asp Ile Thr Asp Glu Ile Asp
                180                 185                 190
Lys Ala Ile Lys Glu Ala Ile Ala Asp Gly Val Lys Leu Asn Glu Leu
                195                 200                 205
Glu Glu Asn Lys Thr Gly Ala Lys Lys Gly Gly Pro Gln Ile Arg Asp
                210                 215                 220
Ala Lys Ile Arg Val Ile Asn Leu Ser Val Lys Phe Leu Lys Glu Ile
225                     230                 235                 240
Glu Glu Glu Ala Asn Ile Leu Lys Asp Asn Val Gly Met Asn Lys Val
                        245                 250                 255
Asp Lys Asp Gln Leu Leu Lys Asp Met Tyr Asp Leu Met Leu Asn Ala
                260                 265                 270
Ala Gly Ser Leu Gln Lys Leu Gly Leu Gln Glu Met Ile Lys Thr Val
                275                 280                 285
Thr Gln Ala Ala Glu Lys Thr Pro Pro Thr Thr Val Glu Gly Ile Leu
                290                 295                 300
Met Ile Ala Asn Thr Ile Glu Asp Lys Leu Lys Lys Ile Lys Gly Lys
305                     310                 315                 320
Gln Glu Thr Asn Lys Lys Asp Glu Ser Ala Lys Gly Pro Asn Leu Thr
                        325                 330                 335
Val Ile Ser Lys Lys Ile Thr Asp Ser Asn Ala Phe Leu Leu Ala Val
                340                 345                 350
Lys Glu Val Glu Ala Leu Leu Ser Ser Ile Asp Glu Leu Ser Lys Ala
                355                 360                 365
Ile Gly Lys Lys Ile Lys Asn Asp Gly Thr Leu Asp Asn Glu Ala Asn
                370                 375                 380
Arg Asn Glu Ser Leu Ile Ala Gly Ala Tyr Glu Ile Ser Lys Leu Ile
385                     390                 395                 400
Thr Gln Lys Leu Ser Val Leu Asn Ser Glu Glu Leu Lys Glu Lys Ile
                        405                 410                 415
Lys Glu Ala Lys Asp Cys Ser Glu Lys Phe Thr Thr Lys Leu Lys Asp
                420                 425                 430
```

```
Ser His Ala Glu Leu Gly Ile Gln Ser Val Gln Asp Asn Ala Lys
        435                 440                 445

Lys Ala Ile Leu Lys Thr His Gly Thr Lys Asp Lys Gly Ala Lys Glu
450                 455                 460

Leu Glu Glu Leu Phe Lys Ser Leu Glu Ser Leu Ser Lys Ala Ala Gln
465                 470                 475                 480

Ala Ala Leu Thr Asn Ser Val Lys Glu Leu Thr Asn Pro Val Val Ala
                485                 490                 495

Glu Ser Pro Lys Lys Pro
                500

<210> SEQ ID NO 14
<211> LENGTH: 506
<212> TYPE: PRT
<213> ORGANISM: Borrelia sp.

<400> SEQUENCE: 14

Met Arg Gly Ser His His His His His His Thr Gly Glu Thr Lys Ile
1               5                   10                  15

Arg Leu Glu Ser Ser Ala Gln Glu Ile Lys Asp Glu Ile Asn Lys Ile
            20                  25                  30

Lys Ala Asn Ala Lys Lys Glu Gly Val Lys Phe Glu Ala Phe Thr Asp
        35                  40                  45

Lys Gln Thr Gly Ser Lys Val Ser Glu Lys Pro Glu Phe Ile Leu Lys
    50                  55                  60

Ala Lys Ile Lys Ala Ile Gln Val Ala Glu Lys Phe Val Lys Ala Ile
65                  70                  75                  80

Lys Glu Glu Ala Glu Lys Leu Lys Lys Ser Gly Ser Ser Gly Ala Phe
                85                  90                  95

Ser Ala Met Tyr Asp Leu Met Leu Asp Val Ser Lys Pro Leu Glu Glu
            100                 105                 110

Ile Gly Ile Gln Lys Met Thr Gly Thr Val Thr Lys Glu Ala Glu Lys
        115                 120                 125

Thr Pro Pro Thr Thr Ala Glu Gly Ile Leu Ala Ile Ala Gln Ala Met
    130                 135                 140

Glu Glu Lys Leu Asn Asn Val Asn Lys Lys Gln Gln Asp Ala Leu Lys
145                 150                 155                 160

Asn Leu Glu Glu Lys Ala Asn Thr Ala Ala Thr Thr Ser Gly Thr Gly
                165                 170                 175

Lys Ala Arg Leu Glu Ser Ser Val Lys Asp Ile Thr Asp Glu Ile Asp
            180                 185                 190

Lys Ala Ile Lys Glu Ala Ile Ala Asp Gly Val Lys Leu Asn Glu Leu
        195                 200                 205

Glu Glu Asn Lys Thr Gly Ala Lys Lys Gly Gly Pro Gln Ile Arg Asp
    210                 215                 220

Ala Lys Ile Arg Val Ile Asn Leu Ser Val Lys Phe Leu Lys Glu Ile
225                 230                 235                 240

Glu Glu Glu Ala Asn Ile Leu Lys Asp Asn Val Gly Met Asn Lys Val
                245                 250                 255

Asp Lys Asp Gln Leu Leu Lys Asp Met Tyr Asp Leu Met Leu Asn Ala
            260                 265                 270

Ala Gly Ser Leu Gln Lys Leu Gly Leu Gln Glu Met Ile Lys Thr Val
        275                 280                 285

Thr Gln Ala Ala Glu Lys Thr Pro Pro Thr Thr Val Glu Gly Ile Leu
```

```
                    290                295                300
Met Ile Ala Asn Thr Ile Glu Asp Lys Leu Lys Lys Ile Lys Gly Lys
305                     310                 315                 320

Gln Glu Thr Asn Lys Lys Gly Ser Gly Gly Asp Glu Ser Ala Lys Gly
                    325                 330                 335

Pro Asn Leu Thr Val Ile Ser Lys Lys Ile Thr Asp Ser Asn Ala Phe
                340                 345                 350

Leu Leu Ala Val Lys Glu Val Glu Ala Leu Leu Ser Ser Ile Asp Glu
            355                 360                 365

Leu Ser Lys Ala Ile Gly Lys Lys Ile Lys Asn Asp Gly Thr Leu Asp
370                 375                 380

Asn Glu Ala Asn Arg Asn Glu Ser Leu Ile Ala Gly Ala Tyr Glu Ile
385                 390                 395                 400

Ser Lys Leu Ile Thr Gln Lys Leu Ser Val Leu Asn Ser Glu Glu Leu
                405                 410                 415

Lys Glu Lys Ile Lys Glu Ala Lys Asp Cys Ser Glu Lys Phe Thr Thr
                420                 425                 430

Lys Leu Lys Asp Ser His Ala Glu Leu Gly Ile Gln Ser Val Gln Asp
                435                 440                 445

Asp Asn Ala Lys Lys Ala Ile Leu Lys Thr His Gly Thr Lys Asp Lys
            450                 455                 460

Gly Ala Lys Glu Leu Glu Glu Leu Phe Lys Ser Leu Glu Ser Leu Ser
465                 470                 475                 480

Lys Ala Ala Gln Ala Ala Leu Thr Asn Ser Val Lys Glu Leu Thr Asn
                485                 490                 495

Pro Val Val Ala Glu Ser Pro Lys Lys Pro
            500                 505
```

<210> SEQ ID NO 15
<211> LENGTH: 1086
<212> TYPE: DNA
<213> ORGANISM: Borrelia sp.

<400> SEQUENCE: 15

```
atgagcctga ccggcaaagc gcgtctggaa agcagcgtga aagatattac caacgaaatt     60
gaaaaagcga ttaaagaagc ggaagatgcg ggcgtgaaaa ccgatgcgtt taccgaaacc    120
cagaccggcg gcaaagtggc gggcccgaaa attcgtgcgg cgaaaattcg tgtggcggat    180
ctgaccatta aatttctgga agcgaccgaa gaagaaacca ttacctttaa agaaaatggc    240
gcgggcgaag atgaatttag cggcatttat gatctgattc tgaacgcggc gaaagcggtg    300
gaaaaaattg gcatgaaaga tatgaccaaa accgtggaag aagcggcgaa agaaaatccg    360
aaaaccaccg cgaacggtat tattgaaatt gtgaaagtga tgaaagcgaa agtggaaaat    420
attaaagaaa aacagaccaa aaaccagaaa aaaaaaaaca ccctgagcgc gattctgatg    480
accctgtttc tgtttattag ctgcaacaac agcggcaaag gcggcgatag cgcgagcacc    540
aacccggcgg atgaaagcgc gaaaggcccg aacctgaccg aaattagcaa aaaaatcacc    600
gatagcaacg cgtttgtgct ggcggtgaaa gaagtggaaa ccctggttct gagcattgat    660
gaactggcga aaaaagcgat tggccagaaa atcgataaca acaacggcct ggcggcgctg    720
aacaaccaga acggcagcct gctggcgggt gcgtatgcga ttagcaccct gattaccgaa    780
aaactgagca aactgaaaaa cctggaagaa ctgaaaaccg aaatcgcgaa agcgaaaaaa    840
tgcagcgaag aatttaccaa caaactgaaa agcggccatg cggatctggg caaacaggat    900
```

```
gcgaccgatg atcatgcgaa agcggcgatt ctgaaaaccc atgcgaccac cgataaaggc    960
gcgaaagaat ttaaagacct gttcgaaagc gtggaaggcc tgctgaaagc ggcgcaggtg   1020
gcgctgacca acagcgtgaa agaactgacc agcccggtgg ttgcggaaag cccgaaaaaa   1080
ccgtaa                                                              1086
```

<210> SEQ ID NO 16
<211> LENGTH: 1113
<212> TYPE: DNA
<213> ORGANISM: Borrelia sp.

<400> SEQUENCE: 16

```
atgaggggat cccatcatca tcatcatcat agcctgaccg gcaaagcgcg tctggaaagc     60
agcgtgaaag atattaccaa cgaaattgaa aaagcgatta aagaagcgga agatgcgggc    120
gtgaaaaccg atgcgtttac cgaaacccag accggcggca aagtggcggg cccgaaaatt    180
cgtgcggcga aaattcgtgt ggcggatctg accattaaat ttctggaagc gaccgaagaa    240
gaaaccatta cctttaaaga aaatggcgcg ggcgaagatg aatttagcgg catttatgat    300
ctgattctga acgcggcgaa agcggtggaa aaaattggca tgaaagatat gaccaaaacc    360
gtggaagaag cggcgaaaga aaatccgaaa accaccgcga acggtattat tgaaattgtg    420
aaagtgatga aagcgaaagt ggaaaatatt aaagaaaaac agaccaaaaa ccagaaaaaa    480
aaaaacaccc tgagcgcgat tctgatgacc ctgtttctgt ttattagctg caacaacagc    540
ggcaaaggcg gcgatagcgc gagcaccaac ccggcggatg aaagcgcgaa aggcccgaac    600
ctgaccgaaa ttagcaaaaa aatcaccgat agcaacgcgt ttgtgctggc ggtgaaagaa    660
gtggaaaccc tggttctgag cattgatgaa ctggcgaaaa aagcgattgg ccagaaaatc    720
gataacaaca acggcctggc ggcgctgaac aaccagaacg gcagcctgct ggcgggtgcg    780
tatgcgatta gcaccctgat taccgaaaaa ctgagcaaac tgaaaaacct ggaagaactg    840
aaaaccgaaa tcgcgaaagc gaaaaaatgc agcgaagaat ttaccaacaa actgaaaagc    900
ggccatgcgg atctgggcaa acaggatgcg accgatgatc atgcgaaagc ggcgattctg    960
aaaacccatg cgaccaccga taaaggcgcg aaagaattta aagacctgtt cgaaagcgtg   1020
gaaggcctgc tgaaagcggc gcaggtggcg ctgaccaaca gcgtgaaaga actgaccagc   1080
ccggtggttg cggaaagccc gaaaaaaccg taa                                1113
```

<210> SEQ ID NO 17
<211> LENGTH: 1053
<212> TYPE: DNA
<213> ORGANISM: Borrelia sp.

<400> SEQUENCE: 17

```
atgaccggcg cgaccaaaat ccgcctggaa cgcagcgcga aagatatcac agatgaaatc     60
gatgcgatca agaaagacgc ggcgctgaaa ggcgtcaact ttgatgcatt taaagataaa    120
aagaccgggt ctggagttag cgagaatcca tttattctgg aagcgaaagt tcgtgctacg    180
acggtggcag aaaaatttgt gattgcgatt gaagaagaag caacgaaact gaaagaaacc    240
ggcagcagtg gcgaatttag tgcgatgtat gacctgatgt ttgaggtctc taaaccgctg    300
cagaaactgg ggattcaaga aatgaccaag acggtatctg atgcagcgga agaaaacccg    360
cctacgacgg cgcaaggcgt cctggaaatt gccaagaaaa tgcgcgaaaa actgcaacgc    420
gttcatacca aaaattattg cactctgaag aagaaagaga atagcacttt tacggatgaa    480
aaatgtaaaa ataataacac cagcgcgaac agcgcggatg aaagcgtgaa aggcccgaac    540
```

```
ctgaccgaaa ttagcaaaaa aatcaccgat agcaacgcgg tgctgctggc ggtgaaagaa    600
gtggaagcgc tgctgagcag cattgatgaa attgcggcga aagcgattgg caaaaaaatc    660
catcagaaca acggcctgga taccgaaaac aaccataacg gcagcctgct ggcgggtgcg    720
tatgcgatta gcaccctgat taaacagaaa ctggatggcc tgaaaaacga aggcttaaaa    780
gaaaaaattg atgcggcgaa aaaatgcagc gaaaccttca ccaacaaact gaaagaaaaa    840
cataccgata gcttcggtaa agaaggcgtg accgacgcgg atgcgaaaga agcgattctg    900
aaaaccaacg gcaccaaaac caaaggcgcg gaagaactgg gcaaactgtt tgaaagcgtg    960
gaagttctga gcaaagcggc caaagaaatg ctggcgaaca gcgtgaaaga actgaccagc   1020
ccggtggtgg cagaatctcc gaaaaagccc taa                                1053
```

<210> SEQ ID NO 18
<211> LENGTH: 1080
<212> TYPE: DNA
<213> ORGANISM: Borrelia sp.

<400> SEQUENCE: 18

```
atgaggggat cccatcatca tcatcatcac accggcgcga ccaaaatccg cctggaacgc     60
agcgcgaaag atatcacaga tgaaatcgat gcgatcaaga aagacgcggc gctgaaaggc    120
gtcaactttg atgcatttaa agataaaaag accgggtctg gagttagcga gaatccattt    180
attctggaag cgaaagttcg tgctacgacg gtggcagaaa aatttgtgat tgcgattgaa    240
gaagaagcaa cgaaactgaa agaaaccggc agcagtggcg aatttagtgc gatgtatgac    300
ctgatgtttg aggtctctaa accgctgcag aaactgggga ttcaagaaat gaccaagacg    360
gtatctgatg cagcggaaga aaacccgcct acgacggcgc aaggcgtcct ggaaattgcc    420
aagaaaatgc gcgaaaaact gcaacgcgtt cataccaaaa attattgcac tctgaagaag    480
aaagagaata gcacttttac ggatgaaaaa tgtaaaaata ataacaccag cgcgaacagc    540
gcggatgaaa gcgtgaaagg cccgaacctg accgaaatta gcaaaaaaat caccgatagc    600
aacgcggtgc tgctggcggt gaaagaagtg gaagcgctgc tgagcagcat tgatgaaatt    660
gcggcgaaag cgattggcaa aaaaatccat cagaacaacg gcctggatac cgaaaacaac    720
cataacggca gcctgctggc gggtgcgtat gcgattagca ccctgattaa acagaaactg    780
gatggcctga aaaacgaagg cttaaaagaa aaaattgatg cggcgaaaaa atgcagcgaa    840
accttcacca acaaactgaa agaaaaacat accgatagct tcggtaaaga aggcgtgacc    900
gacgcggatg cgaaagaagc gattctgaaa accaacggca ccaaaaccaa aggcgcggaa    960
gaactgggca aactgtttga aagcgtggaa gttctgagca aagcggccaa agaaatgctg   1020
gcgaacagcg tgaaagaact gaccagcccg gtggtggcag aatctccgaa aaagccctaa   1080
```

<210> SEQ ID NO 19
<211> LENGTH: 1482
<212> TYPE: DNA
<213> ORGANISM: Borrelia sp.

<400> SEQUENCE: 19

```
atgactggtg aaacgaaaat tcgtctggaa tcatccgctc aggagattaa agacgaaatc     60
aacaaaatta aagcaaacgc caagaaagaa ggcgtgaagt ttgaagcgtt taccgataaa    120
cagaccggca gcaaagtttc agaaaaaccg gagtttattc tgaaagccaa aattaaagcg    180
atccaggttg cggaaaaatt cgtgaaagcg attaaagaag aagccgaaaa actgaaaaaa    240
```

-continued

```
tctggttcga gcggcgcatt ttccgcaatg tatgatctga tgctggatgt aagcaaaccg    300
ctggaagaga ttggcattca gaaaatgacc ggcactgtca caaggaagc ggaaaaaaca     360
ccgccaacca ctgcagaagg gattctggcg atcgcccagg cgatggaaga gaaactgaac    420
aacgttaata aaaacagca ggatgcactg aaaaacctgg aagagaaggc gaacaccgcg     480
gcgactacgt cagggaccgg taaagcgcgt ctggaaagct cggtaaaaga tatcacagac    540
gaaattgaca agccatcaa agaagccatt gcagacggcg ttaaactgaa tgaactggaa     600
gaaaataaaa ccggtgcgaa aaaggtggc ccgcagattc gcgatgcgaa aatccgtgtg     660
atcaacctga gcgttaaatt cctgaaagaa atcgaggagg aagcaaacat cctgaaggat    720
aatgttggca tgaacaaggt agataaagat cagctgctga agacatgta cgacctgatg     780
ctgaacgcgg ctggcagtct gcagaaactg ggtctgcagg aaatgatcaa aacggttacc    840
caagctgcgg aaaaaacccc accgaccacg gttgaaggca ttctgatgat tgcaaacacc    900
attgaagaca aactgaagaa atcaaaggc aaacaggaaa caaacaaaaa agatgaaagc     960
gcaaaaggcc cgaatctgac cgtcatttct aagaaaatta ccgattcaaa cgcgtttctg   1020
ctggccgtga agaggttga agccctgctg tcctcgattg atgaactgag caaagctatc   1080
ggaaagaaaa ttaaaaatga tgggacgctg ataacgagg caaatcgcaa tgaaagcctg   1140
attgcaggcg catatgaaat cagtaaactg attacacaga aactgagtgt cctgaacagc   1200
gaagaactga agaaaaaat caaagaagcc aaagactgtt cggaaaagtt tactaccaaa   1260
ctgaaagact cgcatgctga actgggtatt cagtcagtgc aagatgataa tgcgaaaaaa   1320
gcaattctga aaacgcacgg gacgaaagat aaaggtgcca aagagctgga agaactgttt   1380
aaaagcctgg aatcgctgag taaagccgca caggccgcgc tgaccaatag cgtgaaggaa   1440
ctgactaatc cggttgtagc agaatctccg aaaaagccgt aa                    1482
```

<210> SEQ ID NO 20
<211> LENGTH: 1509
<212> TYPE: DNA
<213> ORGANISM: Borrelia sp.

<400> SEQUENCE: 20

```
atgaggggat cccatcatca ccaccatcat actggtgaaa cgaaaattcg tctggaatca    60
tccgctcagg agattaaaga cgaaatcaac aaaattaaag caaacgccaa gaaagaaggc   120
gtgaagtttg aagcgtttac cgataaacag accggcagca agtttcaga aaaaccggag    180
tttattctga agccaaaaat taagcgatc caggttgcgg aaaaattcgt gaaagcgatt   240
aaagaagaag ccgaaaaact gaaaaaatct ggttcgagcg gcgcattttc cgcaatgtat   300
gatctgatgc tggatgtaag caaaccgctg aagagattg gcattcagaa aatgaccggc   360
actgtcacaa aggaagcgga aaaacaccg ccaaccactg cagaagggat tctggcgatc   420
gcccaggcga tggaagagaa actgaacaac gttaataaaa acagcagga tgcactgaaa   480
aacctggaag agaaggcgaa caccgcggcg actacgtcag ggaccggtaa agcgcgtctg   540
gaaagctcgg taaagatat cacagacgaa attgacaaag ccatcaaaga agccattgca   600
gacggcgtta aactgaatga actggaagaa aataaaaccg gtgcgaaaaa aggtggcccg   660
cagattcgcg atgcgaaaat ccgtgtgatc aacctgagcg ttaaattcct gaaagaaatc   720
gaggaggaag caaacatcct gaaggataat gttggcatga acaaggtaga taaagatcag   780
ctgctgaaag acatgtacga cctgatgctg aacgcggctg gcagtctgca gaaactgggt   840
ctgcaggaaa tgatcaaaac ggttacccaa gctgcgaaa aaaccccacc gaccacggtt   900
```

```
gaaggcattc tgatgattgc aaacaccatt gaagacaaac tgaagaaaat caaaggcaaa    960
caggaaacaa acaaaaaaga tgaaagcgca aaaggcccga atctgaccgt catttctaag   1020
aaaattaccg attcaaacgc gtttctgctg gccgtgaaag aggttgaagc cctgctgtcc   1080
tcgattgatg aactgagcaa agctatcgga aagaaaatta aaaatgatgg gacgctggat   1140
aacgaggcaa atcgcaatga aagcctgatt gcaggcgcat atgaaatcag taaactgatt   1200
acacagaaac tgagtgtcct gaacagcgaa gaactgaaag aaaaaatcaa agaagccaaa   1260
gactgttcgg aaaagtttac taccaaactg aaagactcgc atgctgaact gggtattcag   1320
tcagtgcaag atgataatgc gaaaaaagca attctgaaaa cgcacgggac gaaagataaa   1380
ggtgccaaag agctggaaga actgtttaaa agcctggaat cgctgagtaa agccgcacag   1440
gccgcgctga ccaatagcgt gaaggaactg actaatccgg ttgtagcaga atctccgaaa   1500
aagccgtaa                                                           1509
```

<210> SEQ ID NO 21
<211> LENGTH: 1521
<212> TYPE: DNA
<213> ORGANISM: Borrelia sp.

<400> SEQUENCE: 21

```
atgaggggat cccatcatca ccaccatcat actggtgaaa cgaaaattcg tctggaatca     60
tccgctcagg agattaaaga cgaaatcaac aaaattaaag caaacgccaa gaaagaaggc    120
gtgaagtttg aagcgtttac cgataaacag accggcagca aagtttcaga aaaaccggag    180
tttattctga aagccaaaat taaagcgatc caggttgcgg aaaaattcgt gaaagcgatt    240
aaagaagaag ccgaaaaact gaaaaaatct ggttcgagcg gcgcattttc cgcaatgtat    300
gatctgatgc tggatgtaag caaaccgctg gaagagattg gcattcagaa aatgaccggc    360
actgtcacaa aggaagcgga aaaaacaccg ccaaccactg cagaagggat tctggcgatc    420
gcccaggcga tggaagagaa actgaacaac gttaataaaa aacagcagga tgcactgaaa    480
aacctggaag agaaggcgaa caccgcggcg actacgtcag ggaccggtaa agcgcgtctg    540
gaaagctcgg taaaagatat cacagacgaa attgacaaag ccatcaaaga agccattgca    600
gacggcgtta aactgaatga actggaagaa aataaaaccg gtgcgaaaaa aggtggcccg    660
cagattcgcg atgcgaaaat ccgtgtgatc aacctgagcg ttaaattcct gaaagaaatc    720
gaggaggaag caaacatcct gaaggataat gttggcatga acaaggtaga taaagatcag    780
ctgctgaaag acatgtacga cctgatgctg aacgcggctg gcagtctgca gaaactgggt    840
ctgcaggaaa tgatcaaaac ggttacccaa gctgcggaaa aaaccccacc gaccacggtt    900
gaaggcattc tgatgattgc aaacaccatt gaagacaaac tgaagaaaat caaaggcaaa    960
caggaaacaa acaaaaaagg ttccgggggt gatgaaagcg caaaaggccc gaatctgacc   1020
gtcatttcta agaaaattac cgattcaaac gcgtttctgc tggccgtgaa agaggttgaa   1080
gccctgctgt cctcgattga tgaactgagc aaagctatcg gaaagaaaat taaaaatgat   1140
gggacgctgg ataacgaggc aaatcgcaat gaaagcctga ttgcaggcgc atatgaaatc   1200
agtaaactga ttacacagaa actgagtgtc ctgaacagcg aagaactgaa agaaaaaatc   1260
aaagaagcca aagactgttc ggaaaagttt actaccaaac tgaaagactc gcatgctgaa   1320
ctgggtattc agtcagtgca agatgataat gcgaaaaaag caattctgaa aacgcacggg   1380
acgaaagata aaggtgccaa agagctggaa gaactgttta aaagcctgga atcgctgagt   1440
```

```
aaagccgcac aggccgcgct gaccaatagc gtgaaggaac tgactaatcc ggttgtagca      1500
gaatctccga aaaagccgta a                                                1521
```

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct-Tag
<400> SEQUENCE: 22

His His His His His His
1               5

<210> SEQ ID NO 23
<211> LENGTH: 18
<212> TYPE: DNA
<213> ORGANISM: Artificial Sequence
<220> FEATURE:
<223> OTHER INFORMATION: Synthetic Construct-Tag
<400> SEQUENCE: 23

```
catcatcatc atcatcat                                                      18
```

<210> SEQ ID NO 24
<211> LENGTH: 18
<212> TYPE: DNA
<213> ORGANISM: Artificial Sequence
<220> FEATURE:
<223> OTHER INFORMATION: Synthetic Construct-Tag
<400> SEQUENCE: 24

```
catcatcatc atcatcac                                                      18
```

<210> SEQ ID NO 25
<211> LENGTH: 18
<212> TYPE: DNA
<213> ORGANISM: Artificial Sequence
<220> FEATURE:
<223> OTHER INFORMATION: Synthetic Construct-Tag
<400> SEQUENCE: 25

```
catcatcacc accatcat                                                      18
```

<210> SEQ ID NO 26
<211> LENGTH: 4
<212> TYPE: PRT
<213> ORGANISM: Artificial Sequence
<220> FEATURE:
<223> OTHER INFORMATION: Synthetic Construct-aa+

<400> SEQUENCE: 26

Met Arg Gly Ser
1

<210> SEQ ID NO 27
<211> LENGTH: 12
<212> TYPE: DNA
<213> ORGANISM: Artificial Sequence
<220> FEATURE:
<223> OTHER INFORMATION: Synthetic Construct-aa+

<400> SEQUENCE: 27

```
atgaggggat cc                                                            12
```

-continued

```
<210> SEQ ID NO 28
<211> LENGTH: 4
<212> TYPE: PRT
<213> ORGANISM: Artificial Sequence
<220> FEATURE:
<223> OTHER INFORMATION: Synthetic Construct-linker

<400> SEQUENCE: 28

Gly Ser Gly Gly
1

<210> SEQ ID NO 29
<211> LENGTH: 12
<212> TYPE: DNA
<213> ORGANISM: Artificial Sequence
<220> FEATURE:
<223> OTHER INFORMATION: Synthetic Construct-linker

<400> SEQUENCE: 29
ggttccgggg gt                                                              12

<210> SEQ ID NO 30
<211> LENGTH: 274
<212> TYPE: PRT
<213> ORGANISM: Borrelia sp.

<400> SEQUENCE: 30

Lys Asn Asn Val Gly Gly Asp Asp Lys Lys Asp Thr Ala Ala Ser Ile
1               5                   10                  15

Phe Tyr Gln Ser Ile Ile Asn Leu Gly Asn Gly Phe Ile Glu Val Phe
            20                  25                  30

Asn Ala Phe Ser Gly Leu Val Ala Asp Ala Phe Ser Lys Ala Asp Pro
        35                  40                  45

Lys Lys Ser Asp Val Lys Thr Tyr Phe Asp Ser Ile Thr Lys Thr Leu
    50                  55                  60

Lys Asp Thr Lys Thr Lys Leu Glu Asp Ile Ser Lys Glu Lys Thr Gly
65                  70                  75                  80

Gly Glu Lys Thr Pro Ala Val Glu Gly Ile Ala Glu Val Val Lys Thr
                85                  90                  95

Val Gly Glu Trp Leu Asp Gly Leu Ile Lys Ala Ala Glu Gly Gly Gly
            100                 105                 110

Lys Ala Ala Asp Gly Gly Ser Asp Lys Ile Gly Asn Val Ala Ala
        115                 120                 125

Gly Gly Gly Ala Gly Ala Asp Lys Glu Ser Val Asn Gly Ile Ala Gly
    130                 135                 140

Ala Ile Lys Gly Ile Val Glu Ala Ala Lys Lys Val Glu Gly Val Lys
145                 150                 155                 160

Phe Ala Pro Lys Ala Ala Ala Asp Ala Ala Ala Asp Gly Asn Lys
                165                 170                 175

Lys Ala Gly Lys Leu Phe Gly Thr Ala Ala Gly Ala Asp Ala Gly Asp
            180                 185                 190

Val Lys Asp Ala Ala Ala Ala Val Gly Ala Val Ser Gly Glu Gln Ile
        195                 200                 205

Leu Asn Ala Ile Val Thr Ala Ala Gly Gln Ala Gln Ala Gly Lys
    210                 215                 220

Lys Ala Asp Glu Ala Lys Asn Ala Ile Glu Ala Ile Gly Ala Ala
225                 230                 235                 240

Gly Asp Ala Asp Phe Gly Asp Asp Ile Lys Lys Asn Asp Gln Ile
                245                 250                 255
```

Ala Ala Ala Leu Val Leu Arg Gly Val Ala Lys Asp Gly Lys Phe Ala
            260                 265                 270
Gly Ala

<210> SEQ ID NO 31
<211> LENGTH: 280
<212> TYPE: PRT
<213> ORGANISM: Borrelia sp.

<400> SEQUENCE: 31

Lys Asn Ser Ala Gly Asp Ile Ser Asn Lys Ser Asp Glu Asn Asp Pro
1               5                   10                  15

Thr Thr Leu Phe Tyr Gln Ser Ile Ile Lys Leu Gly Asn Gly Phe Leu
            20                  25                  30

Glu Val Phe Thr Ser Phe Gly Gly Met Val Ala Asp Ala Phe Gly Ala
        35                  40                  45

Lys Trp Glu Ala Lys Lys Ser Thr Ile Lys Thr Tyr Phe Asp Thr Met
50                  55                  60

Ser Gln Lys Leu Glu Glu Thr Lys Lys Gly Leu Glu Lys Leu Ala Asn
65                  70                  75                  80

Asn Gly Glu Glu Ser Glu Ser Glu Asn Lys Ile Gly Asp Ala Val Ala
                85                  90                  95

Ser Thr Ile Lys Glu Val Gly Glu Trp Leu Thr Glu Met Ala Thr Ala
            100                 105                 110

Ala Gly Gly Ala Ala Lys Val Ala Asp Ser Gly Gly Asp Glu Ile Gly
        115                 120                 125

Lys Val Glu Asn Ala Gly Ala Asn Ala Asn Lys Gly Asp Lys Thr Ser
130                 135                 140

Val Asn Gly Ile Ala Lys Gly Ile Lys Ala Ile Val Gly Val Ala Lys
145                 150                 155                 160

Lys Ala Gly Val Lys Trp Glu Pro Ala Ala Ala Glu Ala Gly Asp
                165                 170                 175

Ala Asn Gly Asn Lys Asn Ala Gly Lys Leu Phe Ala Thr Gly Gly Gln
            180                 185                 190

Gly Asp Ala Ala Ala Gly Lys Glu Ala Ala Leu Ala Val Ser Gly Val
        195                 200                 205

Ser Gly Asp Gln Ile Leu Asn Ala Ile Val Thr Asp Ala Glu Gly Asp
    210                 215                 220

Lys Asn Gly Val Ala Thr Ala Asn Ala Thr Asn Ser Ile Asp Ala Ala
225                 230                 235                 240

Ile Gly Ala Asp Gly Asp Asn Gly Ala Ser Gly Phe Asp Ala Met Lys
                245                 250                 255

Lys Lys Asn Asp Lys Ile Ala Ala Ile Val Leu Arg Gly Met Ala
            260                 265                 270

Lys Asp Gly Lys Phe Ala Val Lys
        275                 280

<210> SEQ ID NO 32
<211> LENGTH: 284
<212> TYPE: PRT
<213> ORGANISM: Borrelia sp.

<400> SEQUENCE: 32

Lys Asn Asn Ala Glu Leu Ala Glu Ala Glu Ala Lys Asn Gln Ser Ala
1               5

Lys Asp Phe Tyr His Ala Ile Ile Lys Leu Gly Tyr Gly Phe Val Asp
                20                  25                  30

Val Phe Asn Ala Ile Gly Gly Leu Val Ser Asp Val Phe Tyr Lys Ala
            35                  40                  45

Asp Pro Lys Lys Ser Asp Val Lys Asn Tyr Phe Asp Ser Ile Ala Ser
        50                  55                  60

Ile Leu Lys Glu Thr Gln Thr Lys Leu Asp Ala Leu Ser Lys Glu Gln
65                  70                  75                  80

Gly Gly Gly Asp Gly Thr Gln Val Val Asp Ala Ala Lys Lys Ala
                85                  90                  95

Gly Glu Trp Ile Lys Glu Met His Lys Ala Val Glu Asp Thr Ala Lys
            100                 105                 110

Ala Gly Gly Glu Gly Gly Ser Glu Ser Ile Ala Asn Val Ala Ala Gly
        115                 120                 125

Gly Gly Gly Asn Asp Gly Ala Gly Lys Ala Asp Val Asn Ser Val
            130                 135                 140

Thr Gly Ile Ala Lys Gly Met Lys Ala Ile Val Asp Ala Ala Gly Lys
145                 150                 155                 160

Ala Gly Val Glu Leu Lys Pro Ala Ala Gly Gly Ala Ala Ala Asn
            165                 170                 175

Asp Ala Gly Lys Leu Phe Ala Ser Gly Ala Asn Ala Asn Ala Ala Ala
        180                 185                 190

Asn Ala Asp Asp Ala Glu Gly Ala Ala Glu Ala Ala Gly Lys Ala Val
            195                 200                 205

Ser Ala Val Ser Gly Asp Gln Ile Leu Lys Ala Ile Val Asp Ala Ala
210                 215                 220

Gly Ala Thr Ala Gly Lys Lys Ala Asn Glu Ala Thr Asn Ala Val Glu
225                 230                 235                 240

Ala Ala Ile Gly Asp Asp Asn Ala Gly Gln Ala Gly Ala Ala Phe Ala
            245                 250                 255

Ala Gly Met Gln Asn Lys Asn Asp Gln Ile Ala Ala Ile Val Leu
        260                 265                 270

Arg Gly Leu Ala Lys Ser Gly Lys Phe Ala Asn Glu
        275                 280

<210> SEQ ID NO 33
<211> LENGTH: 279
<212> TYPE: PRT
<213> ORGANISM: Borrelia sp.

<400> SEQUENCE: 33

Lys Asn Asn Ala Val Gly Lys Gly Asn Asp Asp Lys Asp Ser Val Lys
1 5 10 15

Thr Phe Tyr Glu Ser Ile Ile Asn Leu Gly Asn Gly Phe Ile Asp Val
20 25 30

Phe Asn Ala Phe Ser Gly Leu Val Ala Asp Thr Phe Phe Lys Ser Asp
35 40 45

Pro Lys Lys Ser Asp Val Lys Thr Tyr Phe Glu Ser Ile Ser Ser Thr
50 55 60

Leu Lys Ala Thr Lys Gly Lys Leu Asp Glu Leu Val Ser Ala Lys Lys
65 70 75 80

Gly Glu Gly Gly Ser Val Lys Ala Ser Val Glu Ser Ala Val Asp Glu
85 90 95

Val Ser Lys Trp Leu Glu Glu Met Ile Lys Ala Ala Glu Glu Ala Ala
100 105 110

```
Lys Val Gly Gly Thr Gly Gly Asp Gly Lys Ile Gly Asp Ser Ala Ala
        115                 120                 125

Asn His Gly Ala Lys Ala Asp Lys Asp Ser Val Lys Gly Ile Ala Lys
    130                 135                 140

Gly Ile Lys Gly Ile Val Asp Ala Ala Gly Lys Ala Leu Gly Glu Lys
145                 150                 155                 160

Gly Ala Leu Lys Asp Val Lys Ala Ala Ala Asp Asp Glu Ala Asn Ala
                165                 170                 175

Asp Ala Gly Lys Leu Phe Ala Gly Asn Ala Asn Ala Ala Val Gly Ala
            180                 185                 190

Ala Ala Asp Ile Ala Lys Ala Ala Gly Ala Val Thr Ala Val Ser Gly
        195                 200                 205

Glu Gln Ile Leu Lys Ala Ile Val Glu Ala Ala Gly Asp Pro Ala Asn
    210                 215                 220

Gln Ala Gly Lys Lys Ala Glu Glu Ala Lys Asn Pro Ile Ala Ala Ala
225                 230                 235                 240

Ile Gly Thr Asp Asp Asp Asn Gly Ala Ala Phe Lys Asp Glu Met Lys
                245                 250                 255

Lys Ser Asp Lys Ile Ala Ala Ala Ile Val Leu Arg Gly Val Ala Lys
            260                 265                 270

Asp Gly Lys Phe Ala Val Lys
        275

<210> SEQ ID NO 34
<211> LENGTH: 279
<212> TYPE: PRT
<213> ORGANISM: Borrelia sp.

<400> SEQUENCE: 34

Lys Ser Gln Val Ala Asp Lys Asp Asp Pro Thr Asn Lys Phe Tyr Gln
1               5                   10                  15

Ser Val Ile Gln Leu Gly Asn Gly Phe Leu Asp Val Phe Thr Ser Phe
            20                  25                  30

Gly Gly Leu Val Ala Glu Ala Phe Gly Phe Lys Ser Asp Pro Lys Lys
        35                  40                  45

Ser Asp Val Lys Thr Tyr Phe Thr Thr Val Ala Ala Lys Leu Glu Lys
    50                  55                  60

Thr Lys Thr Asp Leu Asn Ser Leu Pro Lys Glu Lys Ser Asp Ile Ser
65                  70                  75                  80

Ser Thr Thr Gly Lys Pro Asp Ser Thr Gly Ser Val Gly Thr Ala Val
                85                  90                  95

Glu Gly Ala Ile Lys Glu Val Ser Glu Leu Leu Asp Lys Leu Val Lys
            100                 105                 110

Ala Val Lys Thr Ala Glu Gly Ala Ser Ser Gly Thr Ala Ala Ile Gly
        115                 120                 125

Glu Val Val Ala Asp Ala Asp Ala Ala Lys Val Ala Asp Lys Ala Ser
    130                 135                 140

Val Lys Gly Ile Ala Lys Gly Ile Lys Glu Ile Val Glu Ala Ala Gly
145                 150                 155                 160

Gly Ser Glu Lys Leu Lys Ala Val Ala Ala Ala Lys Gly Glu Asn Asn
                165                 170                 175

Lys Gly Ala Gly Lys Leu Phe Gly Lys Ala Gly Ala Ala Ala His Gly
            180                 185                 190

Asp Ser Glu Ala Ala Ser Lys Ala Ala Gly Ala Val Ser Ala Val Ser
```

```
                195                 200                 205
Gly Glu Gln Ile Leu Ser Ala Ile Val Thr Ala Ala Asp Ala Ala Glu
    210                 215                 220

Gln Asp Gly Lys Lys Pro Glu Glu Ala Lys Asn Pro Ile Ala Ala Ala
225                 230                 235                 240

Ile Gly Asp Lys Asp Gly Ala Glu Phe Gly Gln Asp Glu Met Lys
                245                 250                 255

Lys Asp Asp Gln Ile Ala Ala Ile Ala Leu Arg Gly Met Ala Lys
            260                 265                 270

Asp Gly Lys Phe Ala Val Lys
        275

<210> SEQ ID NO 35
<211> LENGTH: 25
<212> TYPE: PRT
<213> ORGANISM: Borrelia sp.

<400> SEQUENCE: 35

Met Lys Lys Asp Asp Gln Ile Ala Ala Ile Ala Leu Arg Gly Met
1               5                   10                  15

Ala Lys Asp Gly Lys Phe Ala Val Lys
            20                  25

<210> SEQ ID NO 36
<211> LENGTH: 17
<212> TYPE: PRT
<213> ORGANISM: Borrelia sp.

<400> SEQUENCE: 36

Ile Val Ala Ala Ile Val Leu Arg Gly Val Ala Lys Ser Gly Lys Phe
1               5                   10                  15

Ala

<210> SEQ ID NO 37
<211> LENGTH: 25
<212> TYPE: PRT
<213> ORGANISM: Borrelia sp.

<400> SEQUENCE: 37

Met Lys Lys Asp Asp Gln Ile Ala Ala Ala Met Val Leu Arg Gly Met
1               5                   10                  15

Ala Lys Asp Gly Gln Phe Ala Leu Lys
            20                  25

<210> SEQ ID NO 38
<211> LENGTH: 348
<212> TYPE: PRT
<213> ORGANISM: Borrelia sp.

<400> SEQUENCE: 38

Lys Asn Asn Val Gly Gly Asp Asp Lys Lys Asp Thr Ala Ala Ser Ile
1               5                   10                  15

Phe Tyr Gln Ser Ile Ile Asn Leu Gly Asn Gly Phe Ile Glu Val Phe
            20                  25                  30

Asn Ala Phe Ser Gly Leu Val Ala Asp Ala Phe Ser Lys Ala Asp Pro
        35                  40                  45

Lys Lys Ser Asp Val Lys Thr Tyr Phe Asp Ser Ile Thr Lys Thr Leu
    50                  55                  60

Lys Asp Thr Lys Thr Lys Leu Glu Asp Ile Ser Lys Glu Lys Thr Gly
```

```
                65                  70                  75                  80
Gly Glu Lys Thr Pro Ala Val Glu Gly Ile Ala Glu Val Val Lys Thr
                        85                  90                  95

Val Gly Glu Trp Leu Asp Gly Leu Ile Lys Ala Ala Glu Gly Gly Gly
                100                 105                 110

Lys Ala Ala Asp Gly Gly Ser Asp Lys Ile Gly Asn Val Ala Ala
                115                 120                 125

Gly Gly Gly Ala Gly Ala Asp Lys Glu Ser Val Asn Gly Ile Ala Gly
            130                 135                 140

Ala Ile Lys Gly Ile Val Glu Ala Ala Lys Val Glu Gly Val Lys
145                 150                 155                 160

Phe Ala Pro Lys Ala Ala Asp Ala Ala Ala Asp Gly Asn Lys
                165                 170                 175

Lys Ala Gly Lys Leu Phe Gly Thr Ala Ala Gly Ala Asp Ala Gly Asp
                180                 185                 190

Val Lys Asp Ala Ala Ala Val Gly Ala Val Ser Gly Glu Gln Ile
                195                 200                 205

Leu Asn Ala Ile Val Thr Ala Ala Gly Gln Ala Gly Gln Ala Gly Lys
            210                 215                 220

Lys Ala Asp Glu Ala Lys Asn Ala Ile Glu Ala Ala Ile Gly Ala Ala
225                 230                 235                 240

Gly Asp Ala Asp Phe Gly Asp Ile Lys Lys Asn Asp Gln Ile
                245                 250                 255

Ala Ala Ala Leu Val Leu Arg Gly Val Ala Lys Asp Gly Lys Phe Ala
                260                 265                 270

Gly Ala Met Lys Lys Asp Gln Ile Ala Ala Ile Ala Leu Arg
            275                 280                 285

Gly Met Ala Lys Asp Gly Lys Phe Ala Val Lys Asp Gly Glu Lys Glu
            290                 295                 300

Lys Ala Ile Val Ala Ala Ile Val Leu Arg Gly Val Ala Lys Ser Gly
305                 310                 315                 320

Lys Phe Ala Met Lys Lys Asp Asp Gln Ile Ala Ala Ala Met Val Leu
                325                 330                 335

Arg Gly Met Ala Lys Asp Gly Gln Phe Ala Leu Lys
            340                 345

<210> SEQ ID NO 39
<211> LENGTH: 358
<212> TYPE: PRT
<213> ORGANISM: Borrelia sp.

<400> SEQUENCE: 39

Met Arg Gly Ser His His His His His His Lys Asn Asn Val Gly Gly
1               5                   10                  15

Asp Asp Lys Lys Asp Thr Ala Ala Ser Ile Phe Tyr Gln Ser Ile Ile
                20                  25                  30

Asn Leu Gly Asn Gly Phe Ile Glu Val Phe Asn Ala Phe Ser Gly Leu
            35                  40                  45

Val Ala Asp Ala Phe Ser Lys Ala Asp Pro Lys Lys Ser Asp Val Lys
        50                  55                  60

Thr Tyr Phe Asp Ser Ile Thr Lys Thr Leu Lys Asp Thr Lys Thr Lys
65                  70                  75                  80

Leu Glu Asp Ile Ser Lys Glu Lys Thr Gly Gly Glu Lys Thr Pro Ala
                85                  90                  95
```

-continued

```
Val Glu Gly Ile Ala Glu Val Val Lys Thr Val Gly Glu Trp Leu Asp
            100                 105                 110

Gly Leu Ile Lys Ala Ala Glu Gly Gly Gly Lys Ala Ala Asp Gly Gly
        115                 120                 125

Gly Ser Asp Lys Ile Gly Asn Val Ala Ala Gly Gly Gly Ala Gly Ala
    130                 135                 140

Asp Lys Glu Ser Val Asn Gly Ile Ala Gly Ala Ile Lys Gly Ile Val
145                 150                 155                 160

Glu Ala Ala Lys Lys Val Glu Gly Val Lys Phe Ala Pro Lys Ala Ala
                165                 170                 175

Ala Asp Ala Ala Ala Ala Asp Gly Asn Lys Lys Ala Gly Lys Leu Phe
            180                 185                 190

Gly Thr Ala Ala Gly Ala Asp Ala Gly Asp Val Lys Asp Ala Ala Ala
        195                 200                 205

Ala Val Gly Ala Val Ser Gly Glu Gln Ile Leu Asn Ala Ile Val Thr
    210                 215                 220

Ala Ala Gly Gln Ala Gly Gln Ala Gly Lys Lys Ala Asp Glu Ala Lys
225                 230                 235                 240

Asn Ala Ile Glu Ala Ala Ile Gly Ala Ala Gly Asp Ala Asp Phe Gly
                245                 250                 255

Asp Asp Ile Lys Lys Lys Asn Asp Gln Ile Ala Ala Ala Leu Val Leu
            260                 265                 270

Arg Gly Val Ala Lys Asp Gly Lys Phe Ala Gly Ala Met Lys Lys Asp
        275                 280                 285

Asp Gln Ile Ala Ala Ala Ile Ala Leu Arg Gly Met Ala Lys Asp Gly
    290                 295                 300

Lys Phe Ala Val Lys Asp Gly Glu Lys Glu Lys Ala Ile Val Ala Ala
305                 310                 315                 320

Ile Val Leu Arg Gly Val Ala Lys Ser Gly Lys Phe Ala Met Lys Lys
                325                 330                 335

Asp Asp Gln Ile Ala Ala Ala Met Val Leu Arg Gly Met Ala Lys Asp
            340                 345                 350

Gly Gln Phe Ala Leu Lys
        355
```

<210> SEQ ID NO 40
<211> LENGTH: 1077
<212> TYPE: DNA
<213> ORGANISM: Borrelia sp.

<400> SEQUENCE: 40

```
atgaggggat cccaccacca ccatcatcat aaaaataatg tcggcggcga tgacaaaaaa     60
gatactgcgg ccagcatctt ctaccagtct attattaacc tgggtaacgg gttcattgaa    120
gtgtttaatg ccttttccgg gctggtggcc gacgcgttta gcaaagcaga tccgaaaaaa    180
tcagatgtca aaacttactt cgattcgatc acgaaaacac tgaaagatac caaaactaag    240
ctggaagata ttagcaaaga aaaaacgggc ggcgaaaaaa cgccagccgt tgaaggtatc    300
gccgaagtcg tgaaaaccgt gggagagtgg ctggatggcc tgattaaagc ggcggaaggg    360
ggcggcaaag cggcggatgg tggcggttcg gacaaaattg ggaatgtcgc tgcaggcggc    420
ggcgcgggcg ccgacaagga aagtgtgaat ggaatcgcag gtgccattaa aggtatcgtg    480
gaagctgcaa aaaaggtgga aggtgtgaaa ttcgccccga aagctgcggc ggatgcagcc    540
gccgctgatg gtaacaaaaa agcaggcaaa ctgtttggta ccgcggcggg cgcagacgcg    600
```

-continued

```
ggagacgtga aagatgcagc cgctgcggta ggggccgtga gcggtgaaca gattctgaat    660
gcgattgtta cggcggcggg ccaggcaggc caggcgggga aaaaagctga tgaagcaaaa    720
aatgcgattg aagctgccat tggtgcggct ggcgatgcgg attttggtga cgacattaaa    780
aagaaaaacg atcaaattgc ggcggcgctg gttctgcgcg gagttgctaa agacggcaaa    840
tttgccggcg ctatgaagaa agacgaccaa atcgcggcag ccattgcgct cgcggcatg     900
gcgaaagacg gcaaatttgc ggtgaaagat ggcgaaaaag aaaaagcgat tgtggcggcg    960
atcgttctgc gcggtgttgc gaaaagcggt aaattcgcga tgaaaaaaga tgatcagatc   1020
gccgcagcga tggttctgcg tggtatggcc aaagatggtc agtttgccct gaaataa      1077
```

<210> SEQ ID NO 41
<211> LENGTH: 357
<212> TYPE: PRT
<213> ORGANISM: Borrelia sp.

<400> SEQUENCE: 41

```
Met Gly His His His His His His His Lys Asn Asn Val Gly Gly
1               5                   10                  15

Asp Asp Lys Lys Asp Thr Ala Ala Ser Ile Phe Tyr Gln Ser Ile Ile
            20                  25                  30

Asn Leu Gly Asn Gly Phe Ile Glu Val Phe Asn Ala Phe Ser Gly Leu
        35                  40                  45

Val Ala Asp Ala Phe Ser Lys Ala Asp Pro Lys Lys Ser Asp Val Lys
    50                  55                  60

Thr Tyr Phe Asp Ser Ile Thr Lys Thr Leu Lys Asp Thr Lys Thr Lys
65                  70                  75                  80

Leu Glu Asp Ile Ser Lys Glu Lys Thr Gly Gly Glu Lys Thr Pro Ala
                85                  90                  95

Val Glu Gly Ile Ala Glu Val Val Lys Thr Val Gly Glu Trp Leu Asp
            100                 105                 110

Gly Leu Ile Lys Ala Ala Glu Gly Gly Lys Ala Ala Asp Gly Gly
        115                 120                 125

Gly Ser Asp Lys Ile Gly Asn Val Ala Ala Gly Gly Ala Gly Ala
    130                 135                 140

Asp Lys Glu Ser Val Asn Gly Ile Ala Gly Ala Ile Lys Gly Ile Val
145                 150                 155                 160

Glu Ala Ala Lys Lys Val Glu Gly Val Lys Phe Ala Pro Lys Ala Ala
                165                 170                 175

Ala Asp Ala Ala Ala Asp Gly Asn Lys Lys Ala Gly Lys Leu Phe
            180                 185                 190

Gly Thr Ala Ala Gly Ala Asp Ala Gly Asp Val Lys Asp Ala Ala Ala
        195                 200                 205

Ala Val Gly Ala Val Ser Gly Glu Gln Ile Leu Asn Ala Ile Val Thr
    210                 215                 220

Ala Gly Gln Ala Gly Gln Ala Gly Lys Lys Ala Asp Glu Ala Lys Asn
225                 230                 235                 240

Ala Ile Glu Ala Ala Ile Gly Ala Ala Gly Asp Ala Asp Phe Gly Asp
                245                 250                 255

Asp Ile Lys Lys Lys Asn Asp Gln Ile Ala Ala Ala Leu Val Leu Arg
            260                 265                 270

Gly Val Ala Lys Asp Gly Lys Phe Ala Gly Ala Met Lys Lys Asp Asp
        275                 280                 285

Gln Ile Ala Ala Ala Ile Ala Leu Arg Gly Met Ala Lys Asp Gly Lys
```

```
                    290                 295                 300
Phe Ala Val Lys Asp Gly Glu Lys Glu Lys Ala Ile Val Ala Ala Ile
305                 310                 315                 320

Val Leu Arg Gly Val Ala Lys Ser Gly Lys Phe Ala Met Lys Lys Asp
                325                 330                 335

Asp Gln Ile Ala Ala Ala Met Val Leu Arg Gly Met Ala Lys Asp Gly
                340                 345                 350

Gln Phe Ala Leu Lys
        355

<210> SEQ ID NO 42
<211> LENGTH: 1074
<212> TYPE: DNA
<213> ORGANISM: Borrelia sp.

<400> SEQUENCE: 42
atgggccatc atcatcatca tcatcatcat aaaaacaacg tgggcggcga tgataaaaaa    60
gataccgcgg cgagcatttt ttatcagagc attattaacc tgggcaacgg ctttattgaa   120
gtgtttaacg cgtttagcgg cctggtggcg gatgcgttta gcaaagcgga tccgaaaaaa   180
agcgatgtga aaacctattt tgatagcatt accaaaaccc tgaaagatac caaaaccaaa   240
ctggaagata ttagcaaaga aaaaaccggc ggcgaaaaaa ccccggcggt ggaaggcatt   300
gcggaagtgg tgaaaaccgt gggcgaatgg ctggatggcc tgattaaagc ggcggaaggc   360
ggcggcaaag cggcggatgg cggcggcagc gataaaattg caacgtggc ggcgggcggc    420 ggcgcgggcg cggataaaga aagcgtgaac ggcattgcgg gcgcgattaa aggcattgtg   480
gaagcggcga aaaagtggaa aggcgtgaaa tttgcgccga aagcggcggc ggatgcggcg   540
gcggcggatg caacaaaaa agcgggcaaa ctgtttggca ccgcggcggg cgcggatgcg    600
ggcgatgtga agatgcggc ggcggcggtg ggcgcggtga gcggcgaaca gattctgaac    660
gcgattgtga ccgcgggcca ggcgggccag gcgggcaaaa aagcggatga agcgaaaaac   720
gcgattgaag cggcgattgg cgcggcgggc gatgcggatt ttggcgatga tattaaaaaa   780
aaaaacgatc agattgcggc ggcgctggtg ctgcgcggcg tggcgaaaga tggcaaattt   840
gcgggcgcga tgaaaaaaga tgatcagatt gcggcggcga ttgcgctgcg cggcatggcg   900
aaagatggca aatttgcggt gaaagatggc gaaaaagaaa aagcgattgt ggcggcgatt   960
gtgctgcgcg gcgtggcgaa aagcggcaaa tttgcgatga aaaaagatga tcagattgcg  1020
gcggcgatgg tgctgcgcgg catggcgaaa gatggccagt ttgcgctgaa ataa        1074

<210> SEQ ID NO 43
<211> LENGTH: 7
<212> TYPE: PRT
<213> ORGANISM: Borrelia sp.

<400> SEQUENCE: 43

Asp Gly Glu Lys Glu Lys Ala
1               5
```